United States Patent [19]

Roger et al.

[11] Patent Number: 5,821,255

[45] Date of Patent: *Oct. 13, 1998

[54] BRANCHED-AMINO-SUBSTITUTED THIAZOLES, PROCESSES FOR THEIR PREPARATION AND THE PHARMACEUTICAL COMPOSITIONS WHICH CONTAIN THEM

[75] Inventors: Pierre Marie Albert Roger, Montigny Le Bretonneux; Danièle Anne Jeanne Gully, Muret; Gilles Victor Carlos Courtemanche, St. Martin Du Tertre; Claudie Suzanne Yvette Gautier, Paris; Michel Jacques Henri Geslin, Villeneuve Tolosane; Camille Georges Wermuth, Strasbourg, all of France

[73] Assignee: Sanofi, Paris, France

[*] Notice: The term of this patent shall not extend beyond the expiration date of Pat. No. 5,464,847.

[21] Appl. No.: 756,402

[22] Filed: Nov. 27, 1996

Related U.S. Application Data

[62] Division of Ser. No. 360,351, Dec. 21, 1994, Pat. No. 5,602,132.

[30] Foreign Application Priority Data

Dec. 21, 1993 [FR] France .................................. 93 15386

[51] Int. Cl.⁶ .................................................. A61K 31/425
[52] U.S. Cl. ........................................... 514/342; 514/370
[58] Field of Search ..................................... 514/342, 370

[56] References Cited

U.S. PATENT DOCUMENTS

| | | | |
|---|---|---|---|
| 3,299,087 | 1/1967 | Spivack et al. .................. | 260/306.8 |
| 5,071,864 | 12/1991 | Rendenbach-Mueller et al. .... | 514/370 |
| 5,378,706 | 1/1995 | Biziere et al. ....................... | 514/323.8 |
| 5,464,847 | 11/1995 | Courtemanche ..................... | 514/342 |

FOREIGN PATENT DOCUMENTS

| | | |
|---|---|---|
| 0 283 390 | 3/1988 | European Pat. Off. . |
| 91/09857 | 7/1991 | WIPO . |

OTHER PUBLICATIONS

Sax, N.I. et al. *Hawley's Condensed Chemical Dictionary* (Van Nostrand Reinhold, New York), pp. 21 and 1106 (1987).

Grant, R. et al *Grant & Hackh's Chemical Dictionary* (McGrain–Hill, New York), pp. 14 and 562 (1987).

*Primary Examiner*—Robert Gerstl
*Attorney, Agent, or Firm*—Jacobson, Price, Holman & Stern, PLLC

[57] ABSTRACT

The invention concerns compounds of the formula I:

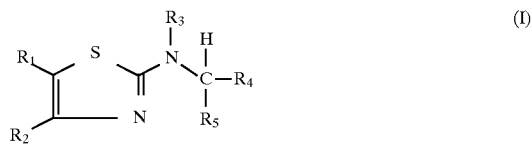

in which $R_1$ to $R_5$ are as defined in claim 1.

These compounds find their application in the treatment of pathologies involving CRF.

3 Claims, No Drawings

BRANCHED-AMINO-SUBSTITUTED THIAZOLES, PROCESSES FOR THEIR PREPARATION AND THE PHARMACEUTICAL COMPOSITIONS WHICH CONTAIN THEM

This is a divisional of application Ser. No 08/360,351, filed Dec. 21, 1994 now U.S. Pat. No. 5,602,132.

The present invention relates to branched-amino-substituted thiazoles, to processes for their preparation and to the pharmaceutical compositions which contain them.

A great number of substituted 2-aminothiazoles is already known. Patent Application EP-0,462,264 describes substituted 2-aminothiazoles the tertiary amine in the 2-position of which contains two substituents each having at least one hetero atom including a substituted amine. These compounds are PAF-acether antagonists and find their applications in the treatment of asthma, of certain allergic or inflamatory conditions, of cardiovascular diseases, of hypertension and of various renal pathologies or alternatively as contraceptive agents. Application GB-2,022,285 describes compounds possessing regulatory activity on the imine response and having anti-inflamatory properties. Theme are thiazole derivatives substituted in the 2-position with secondary amino groups.

Certain heterocyclic substituted 2-acylaminothiazoles have been described in Patent Application EP-0,432,040. These compounds are antagonists of cholecystokinin and of gastrin. Substituted 2-amino-4,5-diphenylthiazoles having anti-inflammatory properties are also known (Patent Application JP-01 75 475). Substituted 2-amino-4-(4-hydrozyphenyl)thiazoles are also known, these being useful a synthesis interodiates for the preparation of substituted 2,2-diarylchloronenothiazoles (Patent Application EP-0, 205,069). Substituted 2-(N-methyl-N-benzylamino) thiazoles are also described in J. Chem. Soc., Perkin Trans 1, (1984), 2, pp. 147–153 and in J. Chem. Soc., Perkin Trans 1, (1983), 2, pp. 341–347.

Patent Application BP-0,283,390 describes, among other substituted thiazolos, substituted 2-[N-alkyl-N-pyridylalkylamino]thiazoles of formula:

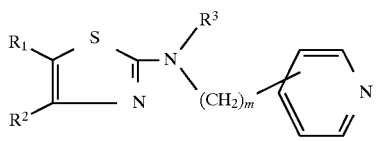

These derivatives, the amine in the 2-position of which is substituted with an unbranched pyridylalkyl radical, are endowed with advantageous pharmacological properties and in particular possess a stimulatory activity on central cholinergic transmission. They may thus be used as miscarine receptor agonists and find their applications in the treatment of memory disorders and of senile dementia.

The compounds of the present invention differ from other substituted 2-aminothiazoles described in the literature, in their novel structure and in their new pharmacological properties. These are substituted 2-aminothiazoles in which the amine in the 2-position is a tertiary amine having a branched aralkyl or alkyl substituent.

This special structure imparts very advantageous pharmacological properties to the products of the invention. Indeed, the compounds of the invention displace, at very low concentrations—below 10 $\mu$M—the binding or $^{125}$I-CRF to the specific receptors present on human and/or mouse brain membranes. The compounds according to the invention will thus modify the effects of CRF, a peptide whose sequence of 41 amino acids was characterized by Vale et al. in 1981. CRF is the main endogenous factor involved in regulation of the hypothalamo-hypophysoadrenal axis (release of adrenocorticotropic hormone: ACTH) and the pathologies thereof, as well as in the depressive syndromes ensuing therefrom. CRF also induces secretion of β-endorphin, of β-lipotropin and of corticosterone. Its specific localization in the limbic regions of the brain and in the locus ceruleus, suggests that this peptide plays an important role in behavioural responses to stress.

Many animal experiments have shown that central administration of CRF induces varied anxiogenic effects such as modification of the behaviour in general: for example neophobia, reduction in sexual receptivity and decrease in food consumption and in slow sleep in rats. Intracerebroventricular injection of CRF also increases excitation of the noradrenergic neurons, which is often associated in animals with a state of anxiety. In rats, central or peripheral administration of CRF induces modifications in gastric emptying, in intestinal transit, in faecal excretion, in acid excretion and in effects on blood pressure.

The specific involvement of CRF in these effects was demonstrated by the use of a peptidic antagonist, alpha-helical CRF(9–41) or of specific antibodies (Rivier J. et al., 1984); it is thus possible to envisage, for this peptide, a role in the establishment of stress-linked endocrine and behavioural disorders.

The repeated administration of CRP in man induces reactions which resemble those described during depression, for example an increase in the emotivity and activity of the sympathetic nervous system, a decrease in the sex drive and the emergence of appetite disorders. Furthermore, the use in man of a test for the stimulation of the HPA axis by CRF is a complementary diagnostic method (Chrousos G. P. et al., 1984), which is a good demonstration of the involvement of CRF in numerous pathologies such as depression, anorexia nervosa and withdrawal from alcohol.

It is also important to point out three possible consequences of states of chronic stress, these being immunodepression, fertility disorders and the onset of diabetes.

The compounds of the invention thus find their application in the treatment of stress-linked diseases and more generally in the treatment of all pathologies involving CRF such as, for eaple, psychiatric disorders, anxiety, anorexia, sexual activity and fertility disorders, immunodepression, gastrointestinal and cardiovascular disorders or the like.

The products of the invention also possess certain advantageous physicochemical characteristics. These are especially products which are soluble in the solvents or solutions usually used in therapy for the oral or parenteral administration of active principles.

More particularly, the subject of the present invention is the compounds of formula I:

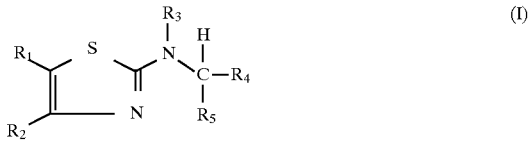

in which,

R$_1$ represents a hydrogen atom or an alkyl radical of 1 to 5 carbon atoms, $R_2$ represents a radical of formula (A):

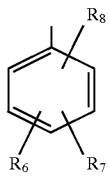

(in which $R_6$ represents a hydroxyalkyl radical of 1 to 5 carbon atoms and $R_7$ and $R_8$, which may be identical or different, each represent a hydrogen atom, a halogen atom or a hydroxyalkyl radical of 1 to 5 carbon atoms, a trifluoromethyl, an alkoxy radical of 1 to 5 carbon atoms or an alkyl radical of 1 to 5 carbon atoms), a radical of formula (B):

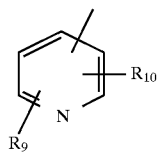

(in which $R_9$ and $R_{10}$, which may of identical or different, each represent a hydrogen atom, a halogen atom, an alkyl radical of 1 to 5 carbon atoms or an alkoxy radical of 1 to 5 carbon atoms), or a radical of formula (C):

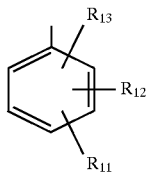

(in which $R_{11}$, $R_{12}$ and $R_{13}$ which may be identical or different, each represent a hydrogen atom, a halogen atom, a trifluoromethyl, an alkoxy radical of 1 to 5 carbon atoms or an alkyl radical of 1 to 5 carbon atoms), $R_3$ represents an alkyl radical of 1 to 5 carbon atoms, a hydroxyalkyl radical of 1 to 5 carbon atoms, a 2-tetrahydropyranyloxyalkyl radical in which the alkyl radical contains from 1 to 5 carbon atoms, an alkoxyalkyl radical of 2 to 10 carbon atoms or an acyloxyalkyl radical of 3 to 11 carbon atoms, $R_4$ represents a cycloalkyl radical of 3 to 6 carbon atoms, a hydroxyalkyl radical of 1 to 5 carbon atoms, an alkoxyalkyl radical of 2 to 10 carbon atoms, a cycloalkyloxyalkyl radical of 4 to 11 carbon atoms, a hydroxyalkyloxyalkyl radical of 2 to 10 carbon atoms, an alcoxyalkyloxyalkyl radical of 3 to 12 carbon atoms, an acyloxyalkyl radical of 3 to 11 carbon atoms or an alkylthioalkyl radical of 2 to 10 carbon atoms, and, $R_5$ represents a cycloalkyl radical of 3 to 6 carbon atoms, a phenyl radical, a thienyl radical or a pyridyl radical (which are optionally substituted with one or more halogen atoms, with alkoxy radicals of 1 to 5 carbon atoms, with alkyl radicals of 1 to 5 carbon atoms or with trifluoromethyl radicals), or a radical of formula (D):

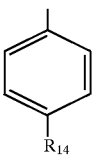

(in which $R_{14}$ represents a carboxyl radical, a carboxyalkyl radical of 2 to 6 carbon atoms, an alkoxycarbonyl radical of 2 to 6 carbon atoms, an acyloxyalkyl radical of 3 to 11 carbon atoms, an alkoxyalkyl radical of 2 to 10 carbon atoms, an aralkoxyalkyl radical of 8 to 16 carbon atoms (which is optionally substituted on the aromatic ring with one or more halogen atoms, alkoxy radicals of 1 to 3 carbon atoms or with trifluoromethyl radicals), a monohalo alkyl radical of 1 to 5 carbon atoms, a linear or branched hydroxyalkyl radical of 1 to 5 carbon atoms, a radical of formula (E):

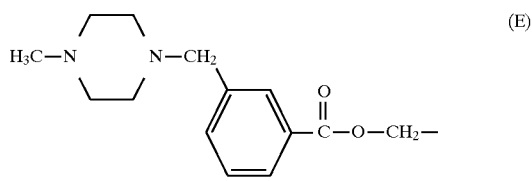

or a sulphoxyalkyl radical of 1 to 5 carbon atoms), a 3-hydroxyalkyl-6-pyridyl radical or a 2-hydroxyalkyl-5-pyridyl radical (in which the alkyl radicals contain from 1 to 5 carbon atoms), on condition, however, that when $R_3$ represents an alkyl radical of 1 to 5 carbon atoms, $R_4$ represents a cycloalkyl radical and $R_5$ represents either a cycloalkyl radical or represents a phenyl radical, a thienyl radical or a pyridyl radical (which are optionally substituted with one or more halogen atoms, with alkoxy radicals of 1 to 5 carbon atoms, with alkyl radicals of 1 to 5 carbon atom or with trifluoromethyl radicals), $R_2$ does not represent a radical of formula (C), the stereoisomers and the addition salts thereof.

Among the preferred compounds of the invention are the compounds of formula I':

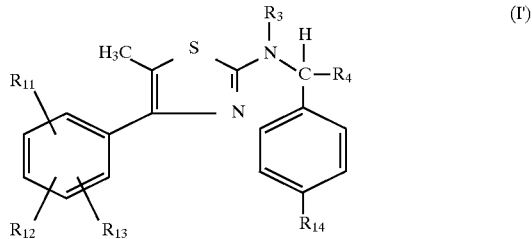

in which, $R_{11}$ represents a halogen atom and $R_{12}$ and $R_{13}$ have the same meaning as for the formula I, $R_3$ represents an alkyl radical of 1 to 5 carbon atoms, $R_4$ represents a cycloalkyl radical of 3 to 6 carbon atoms, and $R_{14}$ has the same meaning as for the formula I, the stereoisomers and the addition salts thereof.

Another group of preferred compounds of the invention corresponds to the formula I":

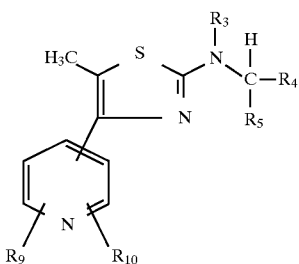

in which
$R_3$, $R_4$, $R_5$, $R_9$ and $R_{10}$ have the meaning given for the formula I,
the stereoisomers and the addition salts thereof.

Among the preferred compound of the invention are also the compounds of formula I''':

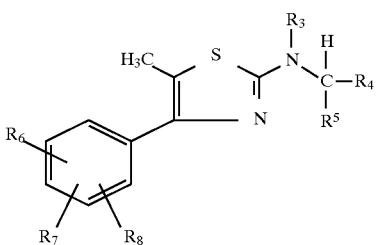

in which,
$R_7$ represents a halogen atom or a ($C_1$–$C_5$) alkoxy, $R_6$ and $R_8$ have the same meaning as for the formula I,
$R_3$ represents an alkyl radical of 1 to 5 carbon atoms, and,
$R_4$ and $R_5$ have the meaning given for the formula I,
the stereoisomors and the addition salts thereof More particularly preferred are the compounds of formula I in which:
$R_1$ represents a hydrogen atom or an alkyl radical of 1 to 5 carbon atoms,
$R_2$ represents a radical of formula (A) or a radical of formula (B),
$R_3$ represents an alkyl radical of 1 to 5 carbon atoms,
$R_4$ represents a cycloalkyl radical of 3 to 6 carbon atoms, and,
$R_5$ represents a cycloalkyl radical of 3 to 6 carbon atoms, a phenyl radical, a thienyl radical or a pyridyl radical (which are optionally substituted with one or more halogen atoms, with alkoxy radicals of 1 to 5 carbon atoms, alkyl radicals of 1 to 5 carbon atoms or trifluoromethyl radicals),
the stereoisomer and the addition salts thereof.

More particularly preferred also are the compounds of formula I in which:
$R_1$ represents a hydrogen atom or an alkyl radical of 1 to 5 carbon atoms,
$R_2$ represents a radical of formula (C),
$R_3$ represents an alkyl radical of 1 to 5 carbon atoms,
$R_4$ represents a cycloalkyl radical of 3 to 6 carbon atoms, and,
$R_5$ represents a radical of formula (D), a 3-hydroxyalkyl-6-pyridyl radical or a 2-hydroxyalkyl-5-pyridyl radical,
the stereoisomers and the addition salts thereof.

The compounds of formula I in which,
$R_1$ represents a hydrogen atom or an alkyl radical of 1 to 5 carbon atoms,
$R_2$ represents a radical of formula (C), $R_3$ represents an alkyl radical of 1 to 5 carbon atoms,
$R_4$ represents a hydroxyalkyl radical of 1 to 5 carbon atoms, an alkoxyalkyl radical of 2 to 10 carbon atoms, a cycloalkyloxyalkyl radical of 4 to 11 carbon atoms, a hydroxyalkyloxyalkyl radical of 2 to 10 carbon atoms, an alkoxyalkyloxyalkyl radical of 3 to 12 carbon atoms, an acyloxyalkyl radical of 3 to 11 carbon atoms or an alkylthioalkyl radical of 2 to 10 carbon atoms,
and,
$R_5$ represents a cycloalkyl radical of 3 to 6 carbon atoms, a phenyl radical, a thienyl radical or a pyridyl radical (which are optionally substituted with one or more halogen atoms, with alkoxy radicals of 1 to 5 carbon atoms, alkyl radicals of 1 to 5 carbon atoms or trifluoromethyl radicals),
the stereoisomers and the addition salts thereof, are also particularly preferred compounds of the invention.

More particularly preferred also are the compounds of formula I in which,
$R_1$ represents a hydrogen atom or an alkyl radical of 1 to 5 carbon atoms,
$R_2$ represents a radical of formula (C),
$R_3$ represents a hydroxyalkyl radical of 1 to 5 carbon atoms, a 2-tetrahydropyranyloxyalkyl radical in which the alkyl radical contains from 1 to 5 carbon atoms, an alkoxyalkyl radical of 2 to 10 carbon atoms or an acyloxyalkyl radical of 3 to 11 carbon atoms,
$R_4$ represents a cycloalkyl radical of 3 to 6 carbon atoms, and,
$R_5$ represents a cycloalkyl radical of 3 to 6 carbon atoms, a phenyl radical, a thienyl radical or a pyridyl radical (which are optionally substituted with one or more halogen atoms, with alkoxy radicals of 1 to 5 carbon atoms, alkyl radicals of 1 to 5 carbon atoms or trifluoromethyl radicals),
the stereoisomers and the addition salts thereof.

The term alkyl radical in understood to refer to linear or branched alkyl radicals of 1 to 5 carbon atoms. This is likewise the case for the alkyl radicals substituted with other radicals such as hydroxyalkyl etc.

The term aralkyl is understood to refer to a radical of formula:

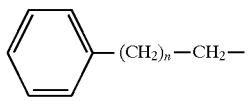

in which n may take values ranging from 0 to 4.

Among the preferred compounds of the invention there may be mentioned the following compounds:
4-(2,4-dichlorophenyl)-5-methyl-2-{N-[α-cyclopropyl-4-(methoxycarbonyl)benzyl]-N-propylamino}thiazole,
4-(2,4-dichlorophenyl)-5-methyl-2-{N-[α-cyclopropyl-4-(hydroxymethyl)benzyl]-N-propylamino}thiazole,
4-(2,4-dichlorophenyl)-5-methyl-2-{N-[α-cyclopropyl-4-(ethoxycarbonyl)benzyl]-N-propylamino}thiazole,
4-(2,4-dichlorophenyl)-5-methyl-2-{N-[α-(acetoxymethyl)benzyl]-N-propylamino}thiazole,
4-(2,4-dichlorophenyl)-5-methyl-2-{N-[α-cyclopropyl-4-(acetoxymethyl)benzyl]-N-propylamino}thiazole,
4-(2,4-dichlorophenyl)-5-methyl-2-{N-[α-cyclopropyl-4-(iodomethyl)benzyl]-N-propylamino}thiazole,
4-(2,4-dichlorophenyl)-5-methyl-2-{N-[α-(methoxymethyl)benzyl]-N-propylamino}thiazole,
4-(2,4-dichlorophenyl)-5-methyl-2-{N-[α-(ethoxymethyl)benzyl]-N-propylamino}thiazole, 4-(2,4-dichlorophenyl)-5-methyl-2-{N-[α-cyclopropyl-4-(1-hydroxy-1-ethyl)benzyl]-N-propylamino}thiazole,
4-(2,4-dichlorophenyl)-5-methyl-2-{N-[α-(hydroxyethyloxymethyl)benzyl]-N-propylamino}thiazole,
4-(2,4-dichlorophenyl)-5-methyl-2-{N-[α-(methoxyethyloxymethyl)benzyl]-N-propylamino}thiazole,
4-(2,4,5-trichlorophenyl)-5-methyl-2-{N-[α-(methoxymethyl)benzyl]-N-propylamino}thiazole,
4-(2,4-dichlorophenyl)-5-methyl-2-{N-[α-(cyclopropyl)-4-(methoxyethyl)benzyl]-N-propylamino}thiazole,
4-(2-methyl-4-chlorophenyl)-5-methyl-2-{N-[α-(methoxymethyl)benzyl]-N-propylamino}thiazole,
4-(2-chloro-4-methylphenyl)-5-methyl-2-{N-[α-(methoxymethyl)benzyl]-N-propylamino}thiazole,
(R)-4-(2-chloro-4-methyloxyphenyl)-5-methyl-2-{N-[α-(methoxymethyl)benzyl]-N-propylamino}thiazole,
(S)-4-(2-chloro-4-methyloxyphenyl)-5-methyl-2-{N-[α-(methoxymethyl)benzyl]-N-propylamino}thiazole,
4-(2,4-dimethoxyphenyl)-5-methyl-2-{N-[α-(methoxymethyl)benzyl]-N-propylamino}thiazole,
4-(2-chloro-4-methoxyphenyl)-5-methyl-2-{N-[α-(methoxymethyl)benzyl]-N-propylamino}thiazole,
4-(2-methoxy-4-chlorophenyl)-5-methyl-2-{N-[α-(methoxymethyl)benzyl]-N-propylamino}thiazole,
4-(2-methoxy-4-methylphenyl)-5-methyl-2-{N-[α-(methoxymethyl)benzyl]-N-propylamino]thiazole,
4-(2-methyl-4-methoxyphenyl)-5-methyl-2-{N-[α-(methoxymethyl)benzyl]-N-propylamino}thiazole,
4-(2-chloro-4-methoxyphenyl)-5-methyl-2-{N-[α-(methoxymethyl)cyclopropylmethyl]-N-propylamino}thiazole,
4-(2-chloro-4-methoxyphenyl)-5-methyl-2-{N-[α-(methylthiomethyl)benzyl]-N-propylamino}thiazole,
4-(2-methoxy-4-chlorophenyl)-5-methyl-2-{N-[α-(methylthiomethyl)benzyl]-N-propylamino} thiazole,
4-(2,5-dichloro-4-methoxyphenyl)-5-methyl-2-{N-[α-(methoxymethyl)benzyl]-N-propylanino}thiazole,
4-(2,5-dichloro-4-methoxyphenyl)-5-methyl-2-{N-[α-(methylthiomethyl)benzyl]-N-propylamino}thiazole,
4-(2,4-dichlorophenyl)-5-methyl-2-{N-[α-(methylthiomethyl)-4-fluorobenzyl]-N-propylamino}thiazole,
4-(2-methyl-4-methoxy-5-chlorophonyl)-5-methyl-2-{N-[α-(methoxymethyl)benzyl]-N-propylamino}thiazole,
4-(2,4-dichlorophenyl)-5-methyl-2-{N-[α-(methoxymethyl)(4-fluorobenzyl)]-N-propylamino}thiazole,
4-(2,4,5-trichlorophenyl)-5-methyl-2-{N-[α-(methoxymethyl)(4-fluorobenzyl)]-N-propylamino}thiazole,
4-(2-methyl-4-methoxy-5-chlorophenyl)-5-methyl-2-{N-[α-(methoxyethyl)(4-fluorobenzyl)]-N-propylamino}thiazole,
4-(2-chloro-4-methoxyphenyl)-5-methyl-2-{N-[α-(methoxymethyl)-4-fluorobenzyl]-N-propylamino}thiazole,
4-(2,4-dichlorophenyl)-5-methyl-2-{N-[α-(methylthiomethyl)benzyl]-N-propylamino}thiazole,
4-(2,4-dichlorophenyl)-5-methyl-2-[N-(1-cyclopropyl-2-methoxy-1-ethyl)-N-propylamino]thiazole,
4-(2,4-dichlorophenyl)-5-methyl-2-{N-[α-(cyclopropylmethoxymethyl)benzyl]-N-propylamino}thiazole,
4-(2,4-dichlorophenyl)-5-methyl-2-{N-[α-(methoxymethyl)benzyl]-N-propylamino}thiazole,
(R)-4-(2,4-dichlorophenyl)-5-methyl-2-{N-[α-(methoxymethyl)benzyl]-N-propylamino}thiazole,
(S)-4-(2,4-dichlorophenyl)-5-methyl-2-{N-[α-(methoxymethyl)benzyl]-N-propylamino}thiazole,
4-(2,4-dichlorophenyl)-5-methyl-2-{N-[α-(methoxymethyl)-2-thienylmethyl]-N-propylamino}thiazole,
4-(2-chloro-4-methoxyphenyl)-5-methyl-2-{N-[α-(methoxymethyl)-2-thienylmethyl]-N-propylamino}thiazole,
4-(2,4-dichlorophenyl)-5-methyl-2-{N-[(α-cyclopropyl)-4-hydroxymethyl-6-pyridylmethyl]-N-propylamino}thiazole.

All these compounds may be in the form of salts.

In free form, the compounds of the invention generally exhibit basic proportion, although there are some which have acidic properties, depending on the substituents.

The salts of the compounds of formula I with pharmaceutically acceptable acids or bases (when this is possible) are the preferred salts, but those which can make it possible to isolate the compounds of formula I and especially to purify them or to obtain pure isomers, are also within the invention.

Among the pharmaceutically acceptable acids for the preparation of addition salts with the compounds of formula I, there may be mentioned hydrochloric acid, phosphoric acid, fumaric acid, citric acid, oxalic acid, sulphuric acid, ascorbic acid, tartaric acid, maleic acid, mandelic acid, methanesulphonic acid, lactobionic acid, gluconic acid, glucaric acid, succinylsulphonic acid, hydroxypropanesulphonic acid, etc.

Among the pharmaceutically acceptable bases for the preparation of addition salts with the compounds of formula I when these have acidic properties, there may be mentioned sodium hydroxide, potassium hydroxide, ammonium hydroxide etc.

Another subject of the present invention is a process for the preparation of the compounds of formula I, characterized in that an alpha-halo-substituted carbonyl compound, preferably an alpha-bromo-substituted carbonyl compound, of formula II:

in which, $R_1$ has the same meaning as for the formula I, $R_{2a}$ represents a radical of formula $(A_a)$:

(in which $R_{6a}$ represents a bromine or iodine atom and $R_{7a}$ and $R_{8a}$, which may be identical or different, each represent a hydrogen atom or a halogen atom), a radical of formula (B) or a radical of formula (C), the radicals (B) and (C) having the same meaning as for the formula I, and, Hal represents a halogen atom, preferably bromine, is reacted either
with a thiourea of formula III$_a$:

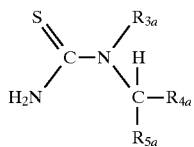 (IIIa)

in which, $R_{3a}$ represents an alkyl radical of 1 to 5 carbon atoms, $R_{4a}$ represents a cycloalkyl radical of 3 to 6 carbon atoms, or a radical of formula (F):

-Alk-O-ProtecA  (F)

(in which Alk represents an alkyl radical of 1 to 5 carbon atoms and ProtecA represents a protecting group which may be removed by acidic hydrolysis, such as a 2-tetrahydropyranyl radical), an alkoxyalkyl radical of 2 to 10 carbon atoms or an alkylthioalkyl radical of 2 to 10 carbon atoms, $R_{5a}$ represents a cycloalkyl radical of 3 to 6 carbon atoms, a phenyl radical, a thienyl radical or a pyridyl radical (which are optionally substituted with one or more halogen atoms, with alkoxy radicals of 1 to 5 carbon atoms, alkyl radicals of 1 to 5 carbon atoms or with trifluoromethyl radicals), a 3-hydroxyalkyl-6-pyridyl radical, a 2-hydroxyalkyl-5-pyridyl radical or a radical of formula (D) in which $R_{14}$ represents a hydroxyalkyl radical of 2 to 5 carbon atoms, in order to form compounds of formula I$_a$:

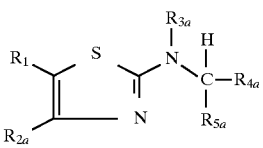 (Ia)

in which, $R_1$ has the same meaning as for the formula I, $R_{2a}$ has the meaning given for the formula II, and $R_{3a}$, $R_{4a}$ and $R_{5a}$ have the meaning given for the formula III$_a$, or with a thiourea of formula III$_b$:

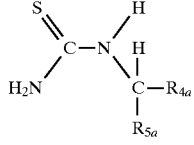 (III$_b$)

in which, $R_{4a}$ and $R_{5a}$ have the same meanings as for the formula III$_a$, in order to form the compounds of formula IV:

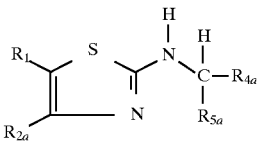 (IV)

in which, $R_1$ has the meaning given for the formula I, $R_{2a}$ has the meaning given for the formula II, and $R_{4a}$ and $R_{5a}$ have the meanings given for the formula III$_a$, which is reacted with a halide of formula V:

Hal-R$_{3b}$  (V)

in which,

Hal represents a halogen atom and, $R_{3b}$ represents an alkyl radical of 1 to 5 carbon atoms or a radical of formula (F), in order to form the compounds of formula I$_b$:

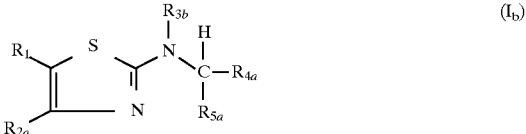 (I$_b$)

in which, $R_1$ has the meaning given for the formula I, $R_{2a}$ has the meaning given for the formula II, $R_{4a}$ and $R_{5a}$ have the meanings given for the formula III$_a$ and, $R_{3b}$ has the meaning given for the formula V, after which, one of the following steps (a) to (d) is performed (a) the compounds of formula I$_a$ and I$_b$, in $R_{2a}$ represents a radical of formula (A$_a$), are subjected:

either to the action of tert-butyllithium and carbon dioxide and then to a reduction to give the compounds of formula I in which $R_2$ represents a radical of formula (A), the substituent $R_6$ and optionally the substituents $R_7$ and/or $R_8$ of which represent a hydroxymethyl radical, or to the action of tert-butyllithium and a ($C_2$–$C_5$) aliphatic aldehyde to give the compounds of formula I in which $R_2$ represents a radical of formula (A), the substituent $R_6$ and optionally the substituents $R_7$ and/or $R_8$ of which represent a linear or branched hydroxyalkyl radical of 2 to 5 carbon atoms, (b) or, either the compounds of formulae I$_a$ and I$_b$, in which $R_{5a}$ represents a 4-bromophenyl radical, are subjected either to the action of an organolithium reagent such as, for example, tert-butyllithium in a suitable ether solvent and to carbon dioxide, to give the compounds of formula I in which $R_5$ represents a 4-carboxyphenyl radical, from which the following are subsequently obtained:

by esterification, the compounds of formula I in which $R_5$ represents a 4-(alkoxycarbonyl)phenyl radical, by reduction, the compounds of formula I in which $R_5$ represents a 4-(hydroxymethyl)phenyl radical, by reduction and then esterification, the compounds of formula I in which $R_5$ represents a 4-(acyloxymethyl)phenyl radical, by reduction and then the action of an alkyl halide or of an aralkyl halide, the compounds of formula I in which $R_5$ represents a 4-(alkoxymethyl)phenyl or 4-(aralkoxymethyl)phenyl radical, by reduction and then by the action of chlorosulphonic acid, the compounds of formula I in which $R_5$ represents a 4-(sulphoxymethyl)phenyl radical, by reduction, the action of 3-chloromethylbenzoyl chloride and then the action of N-methylpiperazine, the compounds of formula I in which $R_5$ represents a radical of formula (D) and $R_{14}$ is a radical of formula (E),
by reduction and then the action of a halogen, the compounds of formula I in which $R_5$ represents a 4-(halomethyl)phenyl radical, or, to the action of tert-butyllithium and to the action of an aliphatic aldehyde to give the compounds of formula I in which $R_5$ represents a 4-(sec-hydroxyalkyl)phenyl radical, or of an aliphatic ketone to give the compounds of formula I in which $R_5$ represents a 4-(tert-hydroxyalkyl)phenyl radical, or the compounds of formulae $I_a$ and $I_b$, in which $R_{5a}$ represents a radical of formula (D) in which $R_{14}$ represents a hydroxyalkyl radical of 2 to 5 carbon atoms, are subjected:
to an esterification to give the compounds of formula I in which $R_5$ represents a 4-(acyloxyalkyl)phenyl radical,
to an alkylation to give the compounds of formula I in which $R_5$ represents a 4-(alkoxyalkyl)phenyl or 4-(aralkoxyalkyl)phenyl radical,
to the action of chlorosulphonic acid to give the compounds of formula I in which $R_5$ represents a 4-(sulphoxyalkyl)phenyl radical,
to the action of a halogen to give the compounds of formula I in which $R_5$ represents a 4-(haloalkyl)phenyl radical, (c) or, the compounds of formulae $I_a$ and $I_b$, in which $R_{4a}$ represents a radical of formula (F), are subjected to a deprotection to give the compounds of formula I in which $R_4$ represents a hydroxyalkyl radical, from which the following are subsequently obtained:
by esterification, the compounds of formula I in which $R_4$ represents an acyloxyalkyl radical,
by alkylation, the compounds of formula I in which $R_4$ represents an alkoxyalkyl or cycloalkyloxyalkyl radical,
by alkylation with protected haloaliphatic alcohols and then deprotection, the compounds of formula I in which $R_4$ represents a hydroxyalkyloxyalkyl radical,
by alkylation wish protected haloaliphatic alcohols, followed by deprotection and then alkylation, the compounds of formula I in which $R_4$ represents an alkoxyalkyloxyalkyl radical, (d) or, the products of formula $I_b$, in which $R_{3b}$ represents a radical of formula (F) are subjected to a deprotection by acid hydrolysis to give the compounds of formula I in which $R_3$ represents a hydroxyalkyl radical, from which are subsequently obtained, by alkylation or by esterification, the compounds of formula I in which $R_3$ represents an alkoxyalkyl radical or an acyloxy alkyl radical respectively, and, if necessary, the compounds of formula I,
are then optionally separated into the possible stereoisomers thereof and/or salified, in order to form the corresponding salts.

The derivatives of formula II may be obtained from the corresponding non-halo ketones of formula $R_{2a}$—CO—$CH_2$—$R_1$, either by the action of bromine in a suitable organic solvent, such as acetic acid, carbon tetrachloride or ethyl ether, or by the action of quaternary ammonium tribromides according to the method described in Bull. Chem. Soc. Japan (1987), 60, pp. 1159–1160 and pp. 2667–2668, or alternatively by the action of cupric bromide in an organic solvent, such as a mixture of chloroform and ethyl acetate (J. Org. Chem. (1964), 29, pp. 3451–3461).

The ketones of formula $R_{2a}$—CO—$CH_3$—$R_1$ are, in general, known and ccmercially available products. These compounds may be prepared by the Friedel-Crafts reaction between a compound of formula $R_{2a}H$ and an acyl halide of formula $R_1CH_2COHal$ (in which Hal represents a halogen atom), preferably an acyl chloride of formula $R_1CH_2COCl$, in the presence of a Lewis acid.

The compounds of formula II, in which $R_{2a}$ represents a radical of formula (C) which is substituted in positions 2 and 4 with a halogen atom, and $R_1$ represents a methyl radical, may be obtained from halo-substituted benzenes and especially by 1,3-dihalobenzenes and alkoxyphenyls, with which 2-bromopropionyl bromide is reacted in the presence of aluminium chloride.

The compounds of formula II, in which $R_{2a}$ represents a 2,6-dihalo-3-pyridyl radical, are obtained either from the corresponding 2,6-dihalo-substituted 3-formylpyridines, with which aliphatic organomagnesium reagents are reacted, to give secondary alcohols substituted in the 1-position with 2,6-dihalo-3-pyridyl radicals, which are then subjected to an oxidation to give the corresponding ketones.

The latter compounds are then converted into bromo ketones of formula II, according to the methods indicated above.

The compounds of formula II in which $R_{2a}$ represents a 2,4-dialkyl-5-pyridyl radical are obtained from substituted 2,4-dialkyl-5-cyanopyridines, with which substituted aliphatic organomagnesium reagents are reacted. (2,4-Dialkyl-5-pyridyl)alkyl ketones are thus obtained, which are then converted into alpha-bromo-substituted carbonyl compounds of formula II.

The compounds of formulae $III_a$ and $III_b$ are obtained from the compounds of formula VI:

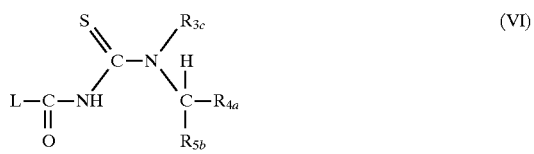

(VI)

in which, $R_{3c}$ has the same meaning as for the formula $III_a$ or represents a hydrogen atom, $R_{4a}$ has the meaning of $R_{4a}$ of the formula $III_a$, $R_{5b}$ has the meaning of $R_{5b}$ of the formula $III_a$ or represents a 2-hydroxyalkyl-5-pyridyl radical, a 3-hydroxyalkyl-6-pyridyl radical or a 4-hydroxyalkylphenyl radical in which the hydrogen of the alcohol group has been replaced with a protecting group which can be rmoved in a basic or acidic medium, depending on the case, and, L represents a phenyl radical or a tert-butyl radical, either by a basic treatment preferably using sodium hydroxide, or by an acidic treatment preferably using hydrochloric acid.

When L is a phenyl radical, the treatment with an inorganic acid is particularly used when $R_{5b}$ in a pyridyl radical which is optionally substituted with one or more halogen atoms, with alkoxy radicals, alkyl radicals or trifluoromethyl radicals.

A basic treatment is performed when $R_4$ is a cycloalkyl group, for example a cyclopropyl, or when $R_{4a}$ represents a radical of formula (F). A basic treatment is also performed when $R_{5b}$ represents either a 2-hydroxyalkyl-5-pyridyl radical or a 3-hydroxyalkyl-6-pyridyl radical or a 4-hydroxyphenyl radical in which the hydrogen of the alcohol group has been replaced with a protecting group which may be removed in a basic or acidic medium, depending on the case.

When L represents a tert-butyl radical, the substituted thioureas of formulae $III_a$ and $III_b$ are obtained from the compounds of formula VI by the action of a strong acid, for example concentrated hydrochloric acid, at a temperature between 10° C. and 100° C.

When $R_{4a}$ represents a radical of formula (F), the compounds of formulae $III_a$ and $III_b$ are obtained from the compounds of formula VI in which $R_{4b}$ represents a hydroxyalkyl radical. Firstly, the hydroxyalkyl radical is protected with a protecting group which may be removed by an acidic hydrolysis and the compounds thus obtained are then subjected to a basic treatment to give the compounds of formulae $III_a$ and $III_b$.

The compounds of formula VI are obtained by reacting benzoyl isothiocyanate or pivaloyl isothiocyanate with the amines of formula VII:

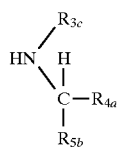

(VII)

in which, $R_{3c}$, $R_{4a}$ and $R_{5b}$ have the same meaning as for the formula VI.

The amines of formula VII, when these are secondary amines, may be prepared by standard methods.

According to a first method, when $R_{3c}$ represents an alkyl radical of 1 to 5 carbon atoms, the corresponding primary amine $VII_a$:

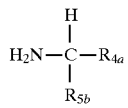

($VII_a$)

is alkylated with an alkyl halide of 1 to 5 carbon atoms, preferably under hot conditions, in the presence of an alkali metal salt in a polar organic solvent, for example dimethylformamide.

According to another alkylation method, the amines of formula $VII_a$ are subjected to the action of an acid halide or of an acid anhydride in an organic solvent chosen from halogenated hydrocarbons, such as methylene chloride, in the presence of a proton acceptor, preferably triethylamine. The amide derived from this reaction is then reduced with hydrides ($LiAlH_4$ or the like) in organic solvents of ether type.

Both methods cited above are preferably used for the preparation of the compounds of formula VII, in the form of pure enantiomers.

Another method for the preparation of the compounds of formula VII consists in coupling a primary Amino of formula $R_{3a}NH_2$ (in which $R_{3a}$ has the same meaning as for the formula $III_a$) with a ketone in a dehydrating medium, in order to form the corresponding imine which is then conventionally reduced with a metal hydride, preferably sodium borohydride, or with hydrogen in the presence of a suitable catalyst. During the reaction of the primary amine of formula $R_{3a}NH_2$ with a ketone in a dehydrating medium, it in preferable to use either titanium IV chloride ($TiCl_4$) or catalysis with paratoluenesulphonic acid.

The amine of formula VII, when $R_{3c}$ represents an alkyl radical of 1 to 5 carbon atoms, are preferably prepared according to a method the principle of which is given in the following scheme:

Step A

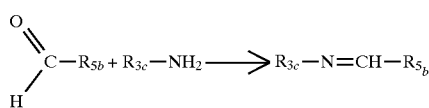

Step B

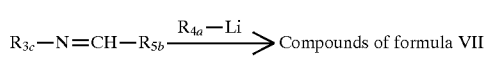

The coupling of the aldehyde with the primary amine in Step A is preferably performed in ethanol or in toluene, at room temperature, and the reaction of the imine with an alkyllithium reagent in Step B is performed in ethyl ether or in tetrahydrofuran, at a temperature between 0° C. and 15° C.

The compounds of the present invention possess highly advantageous pharmacological properties. The compounds of the invention displace, especially at concentrations below $10\,\mu M$ ($0.01$–$10\,\mu M$), the binding of $^{125}I$-CRF to the specific receptors present on rat cortex membranes, according to the method described by De Souza E. B. (J. Neurosci., (1987), 7 (1), pp. 88–100). This is surprising and unexpected, since compounds with a similar structure to that of the compounds of the invention, but in which the amine in the 2-position of the thiazole ring does not contain a branched substituent, do not significantly displace $^{125}I$-CRF binding.

Indeed, 2-[N-methyl-N-(3-pyridylmethyl)amino]-4-(2,4,6-trimethylphenyl)thiazole, the compound described in Example 112 of Patent Application EP-0,283,390, induces a displacement of only about 8%, at the concentration of $10^{-5}M$.

Corticotropic hormone releasing factor (C.R.F.) is a neuropeptide which controls the activity of the hypothalamo-hypophyso-adrenal axis. This factor is responsible for the stress-linked endocrine and behavioural responses.

Indeed, it has been demonstrated that CRF can modify behaviour as well as certain functions of the autonomic nervous system (G. F. Koob, F. E. Bloom, Fed. Proc. (1985), 44, p. 259; M. R. Brown, L. A. Fisher, Fed. Proc. (1985), 44, p. 243). More particularly, CRF induces secretion of corticotropin (ACTH), β-endorphin and other peptides derived from pro-opiomelanocortin (A. Tazi et al., Régul. Peptides (1987) 18, p. 37; M. R. Brown et al., Regul. Peptides (1986) 16, p. 321; C. L. Williams et al., Am. J. Physiol. (1987), G 582, p. 253).

The compounds of the invention may thus be useful for regulating the secretion of these endogenous substances. They find applications more especially as active active principles for medicines for reducing the response to stress (behaviour, emotional states, gastrointestinal and cardiovascular disorders, disorders of the immune system) and more generally in pathologies involving CRF, for example psychiatric disorders, anxiety, anorexia nervosa, sexual activity and fertility disorders, Alzheimer's disease or the like.

The products of the invention are products of very low toxicity. This property makes it possible to envisage sizeable daily doses.

The invention also covers the pharmaceutical compositions containing as active principle at least one compound of general formula I, or one of the salts thereof with a pharmaceutically compatible inorganic or organic acid, in combination with one or more suitable, inert excipients.

The pharmaceutical compositions thus obtained are advantageously provided in various forms such as, for example, tablets, sugar-coated tablets, gelatin capsules, suppositories, and injectable or drinkable solutions.

The active principle may also be provided in the form of a complex with a cyclodextrin, for example α-, β- or γ-cyclodextrin, 2-hydroxypropyl-β-cyclodextrin or methyl-β-cyclodextrin.

The dosage may vary widely depending on the age and weight of the patient, the nature and severity of the complaint and on the route of administration. In general, the unit dosage will be graded between 0.5 mg and 200 mg, and the daily dosage which may be used in human therapy will be graded between 0.5 mg and 800 mg.

The preferred route of administration is the oral or parenteral route.

The examples which follow, given without any limitation being implied, illustrate the invention.

The methods of synthesis of the various intermediates enabling the compounds of the invention to be obtained are described in the various preparations.

The melting points were measured according to the Micro-Köfler technique.

The proton auclear magnetic resonance spectra ($^1$H-NMR) of the compounds of formula I were recorded, depending on the case, at 200 MHz or at 100 MHz.

The microanalyses of the compounds of the invention are in agreement with the theoretical values.

PREPARATIONS

PREPARATION OF THE COMPOUNDS OF FORMULA II

PREPARATION I 2-bromo-1-(2,4-dichlorophenyl)-1-propanone
(Compound 1)

17.4 g of tetra-butylammonium tribromide are added, at room temperature, to 7 g of 1-(2,4-dichlorophenyl)-1-propanone dissolved in a mixture of 420 ml of methylene chloride and 140 ml of methanol. After 24 hours, the reaction medium is evaporated to dryness under vacuum. The residue is taken up in water and extracted with ethyl acetate, and the organic phase is dried over sodium sulphate. The solvent is evaporated off under vacuum and the product is then purified on a column of silica, using a mixture of cyclohexane and ethyl acetate (20:1 v/v) as eluent.

Oil

Yield: 78%

In the same way, it is also possible to obtain 2-bromo-1-(2-chloro-4-methoxyphenyl)-1-propanone (Compound 2).

PREPARATION II 2-bromo-1-(2,4,6-trimethylphenyl)-1-ethanone
(Compound 3)

0.3 mol of 1-(2,4,6-trimethylphenyl)-1-ethanone are dissolved in 200 ml of glacial acetic acid and 31.8 g of bromine are added dropwise, while maintaining the reaction medium at a temperature below 10° C. After the addition, the reaction medium is allowed to return to room temperature and is left at this temperature for 2 hours. The reaction medium is then poured into 500 ml of ice-water and the aqueous phase is extracted with ethyl ether. The organic extracts are washed with saturated aqueous sodium bicarbonate solution and then with salted water, and are dried over anhydrous magnesium sulphate.

After evaporation of the solvent, an oil is obtained which may be used without further purification.

Other compounds (Compounds 4 to 12)

The following compounds were obtained according to the method described for the preparation of 2-bromo-1-(2,4,6-trimethylphenyl)-1-ethanone, using suitable ketones as starting materials.

Compound 4: 2-bromo-1-(2,4-dimethylphenyl)-1-propanone

Compound 5: 2-bromo-1-(4-chloro-2-methylphenyl)-1-propanone

Compound 6: 2-bromo-1-(2-chloro-4-methylphenyl)-1-propanone

Compound 7: 2-bromo-1-(2,4-dimethoxyphenyl)-1-propanone

Compound 8: 2-bromo-1-(4-chlorophenyl)-1-propanone

Compound 9: 2-bromo-1-(2,4-dichlorophenyl)-1-ethanone

Compound 10: 2-bromo-1-(4-methoxyphenyl)-1-propanone

Compound 11: 2-bromo-1-(4-chloro-2-methoxyphenyl)-1-propanone

Compound 12: 2-bromo-1-(4-methylphenyl)-1-propanone

PREPARATION III 2-bromo-1-(2,4,6-trimethoxyphenyl)-1-propanone
(Compound 13)

A suspension of 45.3 g of cupric bromide in 150 ml of ethyl acetate is brought to reflux and 25.1 g of 1-(2,4,6-trimethoxyphenyl)-1-propanone dissolved in 150 ml of chloroform are rapidly added at this temperature. A large amount of greenish-yellow precipitate appears.

The reaction medium is maintained at reflux for 2 hours 30 minutes. It is then allowed to return to room temperature and the insoluble salts are filtered off and washed with ethyl acetate.

The organic phases are treated with charcoal. After removal of the solid by filtration, the solution is concentrated under reduced pressure to give an oil.

The oil is purified by chromatography on a column of silica, using a mixture of cyclohexan and ethyl acetate (6:4 v/v) as eluent.

Oil

Yield: 60%

PREPARATION IV 2-bromo-1-(2,4-dibromophenyl)-1-propanone
(Compound 14)

15 g of aluminium chloride are added with caution, at 0° C., to 25 g of 1,3-dibromobenzene in 250 ml of carbon disulphide, and 22.86 g of 2-bromopropionyl bromide are then run in slowly. The mixture is maintained at reflux for 8 hours, then the carbon disulphide is evaporated off under vacuum and the reaction medium is poured onto crushed ice. The product is extracted twice with heptane, dried, evaporated to dryness and then is purified on a column of silica, using a mixture of cyclohexane and ethyl acetate (10:1 v/v) as eluent, to give the expected product.

Yield: 76%

The process described above may be used and adapted according to known methods in order to prepare 2-bromo-1-(2,4-dichlorophenyl)-1-propanone (Compound 1).

2-Bromo-1-(2-chloro-4-iodophenyl)-1-propanone (Compound 15) was similarly prepared using 1-chloro-3-iodobenzene as starting material instead of 1,3-dibromobenzene. 2-Bromo-1-(4-bromo-2-chlorophenyl)-1-propanone (Compound 16) and 2-bromo-1-(2-bromo-4-chlorophenyl)-1-propanone (Compound 17) were also prepared according to the same process.

The bromo ketones of formula (II) below were prepared using the process described above, using suitable aromatic derivatives and acyl halides as starting materials.

Compound 18: 2-bromo-1-(2,4,5-trichlorophenyl)-1-propanone
Compound 19: 2-bromo-1-(2,3,4-trichlorophenyl)-1-propanone
Compound 20: 2-bromo-1-(2-methoxy-4-methylphenyl)-1-propanone
Compound 21: 2-bromo-1-(2-methyl-4-methoxyphenyl)-1-propanone
Compound 22: 2-bromo-1-(2,5-dichloro-4-methoxyphenyl)-1-propanone
Compound 23: 2-bromo-1-(2-methyl-4-methoxy-5-chloro)-1-propanone
Compound 24: 2-bromo-1-(2,6-difluoro-4-methoxyphenyl)-1-propanone
Compound 25: 2-bromo-1-(2-chloro-4-methoxyphenyl)-1-propanone

PREPARATION V 2-bromo-1-(2,6-dichloro-3-pyridyl)-1-propanone
(Compound 26)

Step A 50 ml of 3M ethylmagnesium bromide solution in ethyl ether are run in, at −70° C., to a solution of 5.2 g of 2,6-dichloro-3-pyridinecarboxaldehyde in 50 ml of ethyl ether. The temperature is allowed to climb to −20° C. and the medium is then hydrolysed. The product is extracted with ethyl ether and then purified on a column of silica, using a mixture of methylene chloride and methanol (99:1 v/v) as eluent.

1-(2,6-Dichloro-3-pyridyl)-1-propanol is thus obtained.
Oil
Yielded 75%

Step B 20 g of activated manganese dioxide are added to a solution of 4.77 g of 1-(2,6-dichloro-3-pyridyl)-1-propanol in 200 ml of methylene chloride. The mixture is heated to reflux for 8 hours and filtered while hot, and the filtrate is evaporated to dryness.

The product is purified on a column of silica, using a mixture of cyclohexane and ethyl acetate (4:1 v/v) as eluent, to give 1-(2,6-dichloro-3-pyridyl)-1-propanone.
Oil
Yield: 65%

Step C

The process is then performed as indicated in Preparation I, using the compound obtained in the above step as ketone, to give 2-bromo-1-(2,6-dichloro-3-pyridyl)-1-propanone.
Oil

PREPARATION VI 2-bromo-1-(2,4-dimethyl-5-pyridyl)-1-propanone
(Compound 27)

Step A 23 g of 2-chloro-3-cyano-4,6-dimethylpyridine are dissolved in 185 ml of concentrated hydrochloric acid and 240 ml of water. 25.4 g of tin metal are added and the mixture is brought to 100° C. The reaction is monitored by thin layer chromatography (TLC). When the reaction is complete, the mixture is allowed to return to room temperature and filtered and the filtrate is neutralized using sodium hydroxide solution. The mixture is extracted with methylene chloride and the combined organic phases are washed with saturated aqueous sodium bicarbonate solution and dried over anhydrous magnesium sulphate. The solution is concentrated to give 5-cyano-2,4-dimethyl-pyridine in the form of a yellow precipitate.

Yield: 54%

Step B 8.91 g of the compound obtained in the above step are suspended in 100 ml of anhydrous ethyl ether, which is cooled to −4° C. 25 ml of 3M ethyl magnesium bromide solution in ethyl ether are added and the mixture is warmed to room temperature. The mixture is hydrolysed with aqueous ammonium chloride solution and extracted with ethyl ether, the solvent is evaporated off and the residue is purified on a column of silica, using methylene chloride as eluent. The eluate is evaporated to dryness to give 1-(2,4-dimethyl-5-pyridyl)-1-propanone in the form of a white powder.

Yield: 43%

Step C

The process is performed as described in Preparation II, using as ketone the ketone obtained in the above step, to give 2-bromo-1-(2,4-dimethyl-5-pyridyl)-1-propanone.
Oil
Yield: 80%

PREPARATION OF THE COMPOUNDS OF FORMULA VII

PREPARATION VII

N-(α-cyclopropylbenzyl)-N-propylamine
(Compound 28)

4 Å molecular sieves and 100 mg of paratoluenesulphonic acid are added to 10 g of cyclopropyl phenyl ketone in 60 ml of anhydrous toluene, followed by 6 g of propylamine. Imine formation is monitored by gas chromatographic assay. After heating for 6 hours at 55° C., the reaction mixture is cooled, the molecular sieves are filtered off and the solution is evaporated to dryness under vacuum. The residue is taken up in 100 ml of anhydrous ethanol. The solution is cooled to 0° C. and 2.65 g of sodium borohydride are added portionwise. After stirring overnight at room temperature, the mixture is evaporated to dryness under vacuum and the residue is taken up in water, hydrolysed with 1N hydrochloric acid in order to bring the pH to 2, and washed with ethyl acetate. The pH is brought to 9 by addition of 2N sodium hydroxide and the mixture is then extracted several times with methylene chloride.

After drying and evaporation of the organic phase, an oil is obtained which may be used directly.

Yield: 60%

Proton nuclear magnetic resonance spectrum (solvent $CDCl_3$): 0.15–1.70 ppm, m, 11H; 2.40 ppm, t+d, 2H; 2.80 ppm, d, 1H; 7.30–7.40 ppm, m, 5H.

Other compounds (Compound, 29 to 39)

The amines indicated in Table I are obtained according to the process described above.

TABLE I

![structure: HN(R3c)-CH(R4a)(R5b)]

| Compounds | R₃c | R₄a | R₅b |
|---|---|---|---|
| 29 | —C₃H₇ | cyclopropyl | cyclopropyl |
| 30 | —C₃H₇ | cyclopentyl | phenyl |
| 31 | —C₃H₇ | cyclopropyl | cyclobutyl |
| 32 | —C₃H₇ | cyclopropyl | 4-Br-phenyl |
| 33 | —C₃H₇ | cyclopropyl | 4-F-phenyl |
| 34 | —C₃H₇ | cyclobutyl | phenyl |
| 35 | —C₃H₇ | cyclopropyl | 4-Cl-phenyl |
| 36 | —C₃H₇ | cyclopropyl | 3-CF₃-phenyl |
| 37 | —C₃H₇ | cyclopentyl | 4-pyridyl |
| 38 | —C₃H₇ | cyclopropyl | 3-Cl-pyridyl |

TABLE I-continued

| Compounds | R₃c | R₄a | R₅b |
|---|---|---|---|
| 39 | —C₃H₇ | —CH₂OCH₃ | 2-pyridyl |

PREPARATION VIII

N-(1-cyclopropyl-2-methoxyethyl)-N-propylamine
(Compound 40)

Step A

A solution of 1.6 ml of cyclopropyl bromide in 30 ml of ethyl ether is added slowly to 1 g of magnesium covered with 10 ml of ethyl ether, while maintaining the temperature of the reaction mixture between 32° C. and 35° C.

The mixture is maintained at reflux for 1 hour and, after cooling to room temperature and filtering over glass wool, the cyclopropylmagnesium bromide solution obtained is then cooled to 0° C. and 2 ml of methoxyacetonitrile diluted in 5 ml of ethyl ether are added. During the addition, the internal temperature rises to 10° C.

After stirring for 15 hours at 20° C., the reaction medium is cooled to 0° C. and poured slowly onto ice-water.

The suspension is stirred vigorously and 12 ml of 30% sulphuric acid are added. After separation of the phases once settling has taken place, the ether phase is washed with aqueous sodium bicarbonate solution and then with saturated aqueous sodium chloride. The solution is dried over anhydrous sodium sulphate and the ethyl ether is evaporated off without heating, to give cyclopropyl methoxymethyl ketone.

Oil

Yield: 98%

Step B 15 ml of molar titanium tetrachloride solution in methylene chloride are added slowly with stirring, at 0° C., to a solution containing 1.7 g of the ketone obtained in the above step and 6.16 ml of N-propylamine in 40 ml of methylene chloride.

After stirring for 15 hours at room temperature, the reaction medium is partially concentrated, diluted with 40 ml of methanol and cooled to 0° C., and 1.14 g of sodium borohydride are added portionwise thereto. After stirring for 24 hours at room temperature, the methanol is evaporated off and the residue is taken up in water and methylene chloride. The white precipitate formed is removed by filtration, the filtrate is extracted with methylene chloride and the organic extracts are washed with saturated aqueous sodium chloride, dried over anhydrous sodium sulphate and evaporated to dryness to give N-(1-cyclopropyl-2-methoxyethyl)-N-propylamine.

Gum

Yield: 74%

The amines described in Table II are obtained according to the process described above according to Preparation VIII (Step A and B or B).

TABLE II

VII

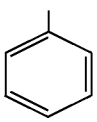

| Compounds | $R_{3c}$ | $R_{4a}$ | $R_{5b}$ |
|---|---|---|---|
| 41 | $-C_3H_7$ | $CH_2OCH_3$ | 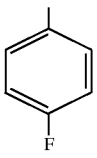 |
| 42 | $-C_3H_7$ | $CH_2OCH_3$ |  |
| 43 | $-C_3H_7$ | $CH_2OCH_3$ |  |
| 44 | $-C_3H_7$ | 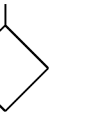 |  |

PREPARATION IX

N-(cyclopropyl-4-pyridylaethyl)-N-prouylamine (Compound 45)

N-(Cyclopropyl-4-pyridylmethyl)-N-propylamine may also be prepared in the following way:

Step A 1.07 g of 4-pyridinecarboxaldehyde are dissolved in 10 ml of absolute ethanol and 0.8 g of N-propylamine are added slowly. After stirring for 30 minutes, the solution is evaporated to dryness to give 1.48 g of oil.

Yield: 99%

Step B

The imine obtained in the above step is dissolved in 10 ml of anhydrous ethyl ether. This solution is added with stirring, at 0° C., to 30 ml of cyclopropyllithium (20 mmol) solution in ethyl ether. After stirring for 2 hours at room temperature, the mixture is cooled to 0° C., followed by dropwise addition of 3 ml of methanol and then 10 ml of aqueous 30% ammonium chloride solution. The ether phase is extracted with 1N hydrochloric acid. The acidic aqueous phase is neutralized with sodium bicarbonate and is then extracted with ethyl acetate.

The organic phase is dried over anhydrous sodium sulphate and evaporated to dryness to give a colourless oil.

Yield: 80%

Proton nuclear magnetic resonance spectrum (solvent CDCl$_3$): 0.28–0.76 ppm, m, 4H; 0.95 ppm, t, 3H; 1.48 ppm, m, 2H; 2.31–2.49 ppm, m, 2H; 2.78 ppm, d, 1H; 7.35 ppm, dd, 2H; 8.54 ppm, dd, 2H.

Other compounds (Compounds 46 to 53)

The amines indicated in Table III are obtained according to the process described above.

TABLE III

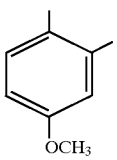

| Compounds | $R_{3c}$ | $R_{4a}$ | $R_{5b}$ |
|---|---|---|---|
| 46 | $-C_3H_7$ |  | 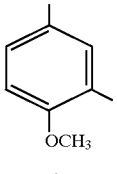 |
| 47 | $-C_3H_7$ |  | 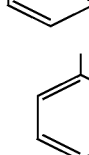 |
| 48 | $-C_3H_7$ | |  |
| 49 | $-C_3H_7$ | | 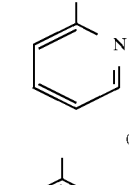 |
| 50 | $-C_3H_7$ | | |
| 51 | $-C_3H_7$ | | |
| 52 | $-C_3H_7$ | | |
| 53 | $-C_3H_7$ | | (1) 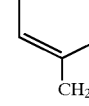 |

(1): MTr represents methoxytrityl

PREPARATION X

α-cyclopropylbenzylaamine (Compound 54)

100 g of cyclopropyl phenyl ketone are stirred in 2,000 ml of methanol with 500 g of pre-dried ammonium acetate and 50 g of sodium cyanoborohydride, in the presence of 4 Å molecular sieves, under argon for 4 days at 50° C. After cooling, the molecular sieves are filtered off and hydrochloric acid is added to bring the pH to 2. The methanol is evaporated to dryness under vacuum and the residue is taken up in diethyl ether. The aqueous phase is washed with ethyl ether and basified by addition of concentrated potassium hydroxide solution so that the pH is above 10. The mixture is extracted twice with methylene chloride and the extracts are washed with saturated sodium chloride solution, dried over anhydrous magnesium sulphate and then concentrated under vacuum to give α-cyclopropylbenzylamine.

Oil

Yield: 76%

PREPARATION XI 2-phenyl-2-(N-propylamino)ethanol (Compound 55)

Step A 24 ml of thionyl chloride are added slowly with stirring, at 0° C., to a suspension of 45.35 g of D,L-phenylglycine in 450 ml of methanol. After stirring for 1 hour at 25° C. and then for 30 minutes at 50° C., the reaction medium is evaporated to dryness. The hydrochloride thus obtained is poured portionwise into 700 ml of saturated aqueous sodium bicarbonate solution. The base formed is extracted with methylene chloride. The organic extract is washed with saturated aqueous sodium chloride, dried over anhydrous sodium sulphate and evaporated to dryness.

Methyl phenylglycinate is thus obtained.

Step B 27 ml of propionyl chloride are added with stirring, at 0° C., to a solution of 44.5 g of the ester obtained in the above step in 350 ml of dimethylformamide and 50 ml of triethylamine. After stirring for 1 hour at room temperature, the reaction medium is poured onto ice and the mixture is then extracted with ethyl acetate. The organic extract is washed with saturated aqueous sodium chloride, dried over anhydrous sodium sulphate and evaporated to dryness to give methyl N-propionylphenylglycinate.

Step C

A solution of 60 g of the compound obtained in the above step in 250 ml of tetrahydrofuran is added slowly with stirring, at 20° C., to a suspension of 41 g of lithium aluminium hydride in 500 ml of anhydrous tetrahydrofuran. After refluxing for 6 hours, the reaction medium is cooled to 0° C. and 200 ml of 15% sodium hydroxide are added thereto with stirring. The mixture is filtered and the filtrate is concentrated under reduced pressure, followed by addition of water and extraction with methylene chloride.

The precipitate contained in the filter is then suspended in 500 ml of 2N hydrochloric acid and is filtered over Celite. The acidic filtrate is washed with ethyl ether and then basified with 30% sodium hydroxide. The precipitate formed is extracted with methylene chloride.

The organic extracts are combined, washed with saturated aqueous sodium chloride, dried over anhydrous sodium sulphate and evaporated to dryness to give 2-phenyl-2-(N-propylamino) ethanol.

Oil

Yield: 91%

Proton nuclear magnetic resonance spectrum (solvent CDCl$_3$): 0.88 ppm, t, 3H; 1,44 ppm, m, 2H; 2.46 ppm, m, 2H; 2.70 ppm, s, 1H; 3.52–3.74 ppm, m, 3H; 7.30 ppm, s, 5H.

By working according to Preparation XI above and using (R)-phenylglycine and (S)-phenylglycine, (R)-2-phenyl-2-(N-propylamino)ethanol (compound 56) and (S)-2-phenyl-2-(N-propylamino)ethanol (compound 57) are respectively obtained.

PREPARATION XII

N-[cyclopropyl-2-(tert-butyldimethylsilyloxymethyl)-5-pyridylmethyl]-N-propylamine (Compound 58)

Step A 17 g of methyl 2-(tert-butyldimethylsilyloxymethyl)-5-pyridinecarboxylate are dissolved in 40 ml of ethyl ether. This solution is added slowly, at 0° C. and under argon, to a solution of 1.62 g of lithium aluminium hydride in 240 ml of ethyl ether. The reaction medium is left stirring for 2 hours at the same temperature. The medium is then hydrolysed by adding 1.6 ml of water, followed by 1.6 ml of 15% sodium hydroxide and 4.8 ml of water. The mixture is filtered and the filtrate is diluted in ethyl acetate. The organic phase is washed with water and dried over anhydrous sodium sulphate. The product is purified on a column of silica, using a mixture of methylene chloride and methanol (97:3 v/v) as eluent.

2-(tert-Butyldimethylsilyloxymethyl)-5-pyridinemethanol is thus obtained.

Oil

Yield: 53%

Step B 8.1 g of the compound obtained in the above step are dissolved in 250 ml of methylene chloride, followed by portionwise addition of 8 g of activated manganese dioxide. The mixture is heated to 40° C. for about 4 hours and the product is then purified on a column of silica, using a mixture of methylene chloride and methanol (99:1 v/v and then 97:3 v/v) as eluent.

2-(tert-Butyldimethylsilyloxymethyl)-5-pyridinecarboxaldehyde is thus obtained.

Oil

Yield: 99%

Step C 70 ml of 0.57N cyclopropyllithium solution are added to 150 ml of ethyl ether and the solution is cooled to −70° C. 8.4 g of the aldehyde obtained in Step B dissolved in ethyl ether are added at the same temperature. The mixture is left stirring for 3 hours, followed by addition, at −70° C., of 3.6 ml of methanol and then water.

The product is extracted with ethyl acetate and then purified on a column of silica, using a mixture of methylene chloride and methanol (97:3 v/v) as eluent.

Cyclopropyl-2-(tert-butyldimethylsilyloxymethyl)-5-pyridinemethanol is thus obtained.

Yield: 55%

Step D 5.44 g of the compound obtained in Step C are dissolved in 170 ml of methylene chloride and 14 g of activated manganese dioxide are added portionwise thereto. The mixture is maintained at reflux for 4 hours. The product is purified on a column of silica, using a mixture of methylene chloride and methanol (99:1 v/v) as eluent, to give cyclopropyl 2-(tert-butyldimethylsilyloxymethyl)-5-pyridyl ketone.

Oil

Yield: 88%

Proton nuclear magnetic resonance spectrum (solvent CDCl$_3$): 0.03 ppm, s, 6H; 0,85 ppm, s, 9H; 0.80–1.20 ppm, m, 4H; 2.55 ppm, m, 1H; 4.83 ppm, s, 2H; 7.56 ppm, d, 1H; 8.23 ppm, dd, 1H; 9.08 ppm, d, 1H.

Step E 4.76 g of the ketone obtained in the above step are dissolved in 100 ml of methanol. 12.6 g of ammonium acetate, 1.83 g if sodium cyanoborohydride and 4 Å molecular sieves are added at room temperature. The mixture is heated at 55° C. for 48 hours, followed by removal of the molecular sieves by filtration, washing with methylene chloride and evaporation to dryness. The residue is taken up in water and extracted with methylene chloride.

The product is purified on a column of silica, using a mixture of methylene chloride and methanol (96:4 v/v) as eluent, to give cyclopropyl-[2-(tert-butyldimethylsilyloxymethyl)- 5-pyridyl]methylamine.
Oil
Yield: 54%

Step F 0.93 g of the amine obtained in the above step is introduced into 40 ml of toluene containing molecular sieves (4 Å). 0.9 ml of propionaldehyde is added. The mixture is heated to 37° C. and is allowed to cool to room temperature and then left stirring for 2 hours, filtered under argon and washed with methylene chloride. The solvents are evaporated off and the residue is taken up in methanol.

0.15 g of sodium borohydride is added at 0° C. and the mixture is left stirring for about 1 hour 30 minutes. While still at 0° C., a few drops of water are added and the solvent is partially evaporated off. The residue is taken up in methylene chloride and the organic phase is washed with water and dried over anhydrous sodium sulphate.

The product is purified on a column of silica, eluting with a mixture of methylene chloride and methanol (97:3 v.v).
Oil
Yield: 91%

Proton nuclear magnetic resonance spectrum (solvent CDCl$_3$): 0.07 ppm, s, 6H; 0.10–1.05 ppm, m, 17H; 1.05–1.80 ppm, m, 2H; 2.20–2.40 ppm, m, 2H; 2.77 ppm, d, 1H; 4.78 ppm, s, 2H; 7.42 ppm, d, 1H; 7.69 ppm, dd, 1H; 8.37 ppm, d, 1H.

PREPARATION XII(BIS)

N-[cyclopropyl-3-(p-anisyldiphenylmethyloxymethyl)-6-pyridylmethyl]-N-propylamine (Compound 53)

Step A 22 g of 2-(tert-butyldimethylsilyloxymethyl)-5-pyridinemethanol are dissolved in 100 ml of anhydrous pyridine. 32 g of p-anisylchlorodiphenylmethane are added thereto at 0° C. under argon. The reaction mixture is left stirring for 3 hours at room temperature. The mixture is evaporated to dryness and the residue is then taken up in water and extracted with ethyl acetate. The organic phase is dried over anhydrous sodium sulphate. The product is purified on a column of silica, using cyclohexane and ethyl acetate (9:1 v/v) as eluent.

The corresponding trityl derivative is thus obtained.
Yield: 95%

Step B 50 g of the compound obtained above are dissolved in 800 ml of tetrahydrofuran. 100 ml of tetrabutylammonium fluoride solution are added dropwise at room temperature. After stirring for 16 hours at room temperature, the solvent is evaporated off. The residue is taken up in methylene chloride. The organic phase is washed with water, dried over sodium sulphate and then evaporated to dryness. The product is purified on a column of silica, using methylene chloride and methanol (99:1 v/v and then 92:8 v/v) as eluent.

3-(p-Anisyldiphenylmethyloxymethyl)-6-pyridinemethanol is thus obtained.
Yield: 85%

Step C 27.8 g of the above compound are dissolved in 500 ml of methylene chloride. 24 g of activated manganese dioxide are added portionwise thereto. The mixture is heated at 50° C. for 8 hours. The product is purified on a column of silica, using a mixture of methylene chloride and methanol (92:8 v/v) as eluent.

3-(p-Anisyldiphenylmethyloxymethyl)-6-pyridinecarboxaldehyde is thus obtained.
Yield: 70%

This compound leads, according to Preparation IX steps A and B, to the expected amine.

PREPARATION XIII

N-[α-cyclopropyl-4-(tert-butyldimethylsilyloxyethyl)benzyl]-N-propylamine (Compound 59)

Step A 5 g of 2-(4-cyanophenyl)ethanol are introduced into 50 ml of dimethylformamide 2.54 g of imidazole, 5,63 g of tert-butyldimethylsilyl chloride and a spatula tip-ful of dimethylaminopyridine are added. The reaction medium is left for 2 hours at room temperature and is then added to an ice-water mixture. The mixture is extracted with ethyl acetate and the extracts dried over anhydrous sodium sulphate. The product is purified by chromatography on a column of silica gel, using a mixture of cyclohexane and ethyl acetate (10:1 v/v) as eluent, to give 1-cyano-4-(tert-butyldimethylsilyloxyethyl)benzene.

Step B 10 g of the compound obtained in Step A are dissolved in 200 ml of tetrahydrofuran and the solution is cooled to between –60° C. and –70° C. 90 ml of a 0.57M solution, at 0° C., of cyclopropyllithium in ethyl ether are added and stirring is maintained for 2 hours. the mixture is hydrolysed at –60° C. by addition of 10 ml of methanol and 10 ml of aqueous 35% ammonium sulphate solution. This mixture is then extracted with ethyl acetate and the extracts dried over anhydrous sodium sulphate. The product is purified by chromatography on a column of silica, eluting with a gradient of ethyl acetate in cyclohexane (2.5 to 20%).

Cyclopropyl 4-(tert-butyldimethylsilyloxyethyl)phenyl ketone is thus obtained.
Yield: 77.4%

Proton nuclear magnetic resonance spectrum (solvent CDCl$_3$): 0.04 ppm, s, 6H; 0.84 ppm, s, 9H; 0.90–1.10 ppm, m, 2H; 1.15–1.30 ppm, m, 2H; 2.60–2.70 ppm, m, 1H; 2.85 ppm, t, 2H; 3.82 ppm, t, 2H; 7.29 ppm, d, 2H; 7.93 ppm, d, 2H.

Step C

The process is performed as indicated in Preparation VIII, Step B, using the compound obtained in the above step as ketone, to give N-[α-cyclopropyl-4-(tert-butyldimethylsilyloxyethyl)benzyl]-N-propylamine.
Yield: 87%

Proton nuclear magnetic resonance spectrum (solvent CDCl$_3$): 0.05 ppm, s, 6H; 0.20–1.20 ppm, m, 17H; 1.20–1.60 ppm, m, 2H; 2.40 ppm, t, 2H; 2.79 ppm, m, 3H; 3.79 ppm, t, 2H; 7.10–7.30 ppm, m, 4H.

PREPARATION XIV

N-[cyclopropyl-(2-methyl-4-pyridyl)methyl]-N-propylamine (Compound 60)

Step A 130 ml of 0.7M cyclopropyllithium solution in diethyl ether are added, at –65° C., to 7.3 g of 4-cyano-2-methylpyridine in 100 ml of anhydrous tetrahydrofuran. After stirring for 4 hours, methanol and ammonium sulphate solution (6.39 g in 20 ml of water) are added. After extraction with ethyl ether, the organic phase is washed with water, dried and evaporated under vacuum. The residue is purified on a column of silica, using a mixture of methylene chloride and methanol (98:2 v/v) as eluent.

Cyclopropyl 2-methyl-4-pyridyl ketone is thus obtained.
Yield 59%

Proton nuclear magnetic resonance spectrum (solvent CDCl$_3$): 0.94–1.38 ppm, m, 4H; 2.62 ppm, s, 3H; 2.52–2.65 ppm, m, 1H; 7.57 ppm, m, 2H; 8.65 ppm, d, 1H.

Step B

The process is performed according to the method described in Preparation VII, using the ketone obtained in the above step, to give N-[cyclopropyl-(2-methyl-4-pyridyl)methyl]-N-propylamine.

PREPARATION XV

N-[α-(methoxyethyl)benzyl]-N-propylamine
(Compound 61)

Step A

A solution of 7.6 ml of chloromethyl methyl ether in 20 ml of carbon tetrachloride is stirred, at about 20° C., with 121 mg of anhydrous zinc chloride, and 11.5 ml of styrene dissolved in 20 ml of carbon tetrachloride are added over 40 minutes. The reaction medium is stirred for 1 hour 30 minutes at room temperature, followed by addition of 10 ml of water and 10 ml of 1N sodium hydroxide. The organic phase is washed with saturated aqueous sodium chloride, dried over anhydrous sodium sulphate and evaporated to dryness.

α-Chloro-α-(methoxyethyl)toluene is thus obtained.
Yield: 93%

Step B

A solution containing 15.5 g of the compound obtained in step A in 30 ml of dimethylformamide is stirred with 34.4 ml of N-propylamine and 14 ml of triethylamine at 60° C. for 15 hours, then the temperature of the reaction medium is adjusted to 80° C. and the mixture is left stirring for 3 hours.

The excess N-propylamine is then evaporated off under reduced pressure and the reaction medium is diluted in 400 ml of ethyl acetate. The organic phase is washed with water and then depleted with three times 150 ml of 2N hydrochloric acid. The acidic aqueous phases are basified, at 0° C., with 30% sodium hydroxide. After extraction with methylene chloride, washing of the organic extract with water, with saturated aqueous sodium chloride and evaporation to dryness, N-[α-(methoxyethyl)benzyl]-N-propylamine is obtained.

Oil
Yield: 50%

Proton nuclear magnetic resonance spectrum (solvent CDCl$_3$): 0.82 ppm, t, 3H; 1.30–1.60 ppm, m, 2H; 1.78–2.05 ppm, m, 2H; 2.36 ppm, m, 2H; 3.20–3.35 ppm, m+s, 5H; 3.71 ppm, t, 1H; 7.26 ppm, s, 5H.

PREPARATION XVI

N-[α-(methylthiomethyl)benzyl]-N-propylamine
(Compound 62)

Step A

A solution of 21.4 g of bromoacetophenone is added to 90 ml of ethanol at 0° C., followed by slow addition of a solution of 5 g of sodium thiomethoxide in 25 ml of water. The reaction medium is stirred for one hour at 0° C. and then for 2 hours at room temperature, and is subsequently poured on to 500 ml of ice-water and extracted with twice 200 ml of ethyl ether. The ether phases are combined and washed with saturated aqueous sodium chloride, dried over anhydrous sodium sulphate and then evaporated to dryness. The residue is distilled to give 2-(methylthio)acetophenone.
Yield: 74%

Step B

The process is performed as described in Preparation VII, using the compound obtained in the above step as ketone. N-[α-(Methylthiomethyl)benzyl]-N-propylamine is thus obtained.

Oil
Yield: 58%

Proton nuclear magnetic resonance spectrum (solvent CDCl$_3$): 0.87 ppm, m, 3H; 1.40 ppm, m, 2H; 2.05 ppm, s, 3H; 2.12 ppm, m, 2H; 2.70 ppm, m, 2H; 3.72 ppm, m, 1H; 7.26–7.37 ppm, m, 5H.

By working according to Preparation XVI above, N-[α-(methylthiomethyl)-4-fluorobenzyl]-N-propylamine (Compound 63) was also prepared.

PREPARATION OF THE COMPOUNDS OF FORMULAE III$_a$ AND III$_b$

PREPARATION XVII

N-(α-cyclopropyl-4-bromobenzyl)-N-propylthiourea
(Compound 64)

Step A

N'-benzoyl-N-(α-cyclopropyl-4-bromobenzyl)-N-propylthiourea 10.15 g of ammonium thiocyanate are suspended in 60 ml of acetone and the suspension is cooled to 0° C. 14.2 ml of benzoyl chloride dissolved in 15 ml of acetone are slowly added thereto. The mixture is left stirring for 15 minutes, followed by addition of 29 g of N-(α-cyclopropyl-4-bromobenzyl)-N-propylamine (Compound 32). The mixture is allowed to return to room temperature and stirring is continued for 2 hours. 20 ml of water are then added, followed by concentrating to the maximum extent. The residue is taken up in a mixture of water and methylene chloride. The organic phase is dried over anhydrous sodium sulphate and then concentrated and allowed to stand, to give the expected product in the form of yellow crystals.

Yield: 87%

Step B 220 ml of 1N sodium hydroxide are added to 38 g of the compound obtained in the above step dissolved in 550 ml of methanol, and the mixture is maintained at reflux for 24 hours. The methanol is evaporated off and the residue extracted with methylene chloride. The organic phase is dried over anhydrous sodium sulphate and evaporated under vacuum. The residue is purified by chromatography on a column of silica, using a mixture of cyclohexane and ethyl acetate (7:1 v/v) as eluent.

N-(α-Cyclopropyl-4-bromobenzyl)-N-propylthiourea is thus obtained in the form of a white powder.

Proton nuclear magnetic resonance spectrum (solvent CDl$_3$): 0.4–1.0 ppm, m, 7H; 1.0–1.4 ppm, m, 1H; 1.6–1.8 ppm, m, 2H; 2.9–3.2 ppm, m, 3H; 5.8 ppm, m, 2H; 7.2–7.5 ppm, m, 4H.

Other compounds (Compounds 65 to 95)

The thiourea derivatives indicated in Table IV are obtained according to the process described for N-(α-cyclopropyl-4-bromobenzyl)-N-propylthiourea, using suitable amines, the preparation of which is indicated above (preparation of the compounds of formula VII), or using commercially available amines.

TABLE IV

Structure VII: thiourea H2N-C(=S)-N(R3c)-CH(R4a)(R5a), R3c = R3a or H

| Compounds | R3c | R4a | R5a |
|---|---|---|---|
| 65 | —C3H7 | cyclopropyl | phenyl |
| 66 | —C3H7 | cyclopropyl | cyclopropyl |
| 67 | —C3H7 | cyclopentyl | phenyl |
| 68 | —C3H7 | cyclopropyl | cyclobutyl |
| 69 | —C3H7 | cyclopropyl | 4-F-phenyl |
| 70 | —C3H7 | cyclobutyl | phenyl |
| 71 | —C3H7 | cyclopropyl | 4-Cl-phenyl |
| 72 | —C3H7 | cyclobutyl | cyclobutyl |
| 73 | —C3H7 | cyclopropyl | cyclopentyl |
| 74 | H | cyclopropyl | phenyl |
| 75 | —C3H7 | —CH2OCH3 | cyclopropyl |
| 76 | —C3H7 | cyclopropyl | 3,4-dimethoxyphenyl |
| 77 | —C3H7 | cyclopropyl | 4-pyridyl |
| 78 | —C3H7 | cyclopropyl | 3-CF3-phenyl |
| 79 | —C3H7 | cyclopropyl | 3-Cl-4-pyridyl |
| 80 | —C3H7 | cyclopropyl | 2,4-dimethoxyphenyl |
| 81 | —C3H7 | cyclopropyl | 2,4-dichlorophenyl |
| 82 | —C3H7 | cyclopropyl | 3-methylphenyl |
| 83 | —C3H7 | cyclopropyl | 4-I-phenyl |
| 84 | —C3H7 | cyclopropyl | 2-pyridyl |
| 85 | —C3H7 | cyclopropyl | 2-methyl-4-pyridyl |

TABLE IV-continued $$\underset{H_2N}{\overset{S}{\underset{\parallel}{C}}} - N \overset{R_{3c}}{\underset{\underset{R_{5a}}{|}}{\overset{|}{\underset{\parallel}{C}}}} - R_{4a} \qquad R_{3c} = R_{3a} \text{ or } H \qquad \text{VII}$$

| Compounds | $R_{3c}$ | $R_{4a}$ | $R_{5a}$ |
|---|---|---|---|
| 86 | $-C_3H_7$ | $-C_2H_4OCH_3$ | phenyl |
| 87 | $-C_3H_7$ | $-CH_2SCH_3$ | phenyl |
| 88 | $-C_3H_7$ | $-CH_2OCH_3$ | phenyl |
| 89 | $-C_3H_7$ | cyclopropyl | pyridyl-CH₂OH (1) |
| 90 | $-C_3H_7$ | $-CH_2OCH_3$ | pyridyl (1) |
| 91 | $-C_3H_7$ | $-CH_2SCH_3$ | 4-fluorophenyl |
| 92 | $-C_3H_7$ | $-CH_2OCH_3$ | 4-fluorophenyl |
| 93 | $-C_3H_7$ | $-CH_2OTHP$ (2) | phenyl (R) |
| 94 | $-C_3H_7$ | $-CH_2OTHP$ (2) | phenyl (S) |
| 95 | $-C_3H_7$ | $-CH_2OCH_3$ | thienyl |

$^{(1)}$: For the deprotections: 1) para-toluenesulphonic acid, 2) sodium hydroxide
$^{(2)}$: THP represents tetrahydropyranyl

PREPARATION XVIII

N-[α-(2-tetrahydropyranyloxymethyl)benzyl]-N-propylthiourea (Compound 96)

Step A

N'-benzoyl-N-(α-hydroxymethylbenzyl)-N-propylthiourea

The process is performed as described in Preparation XVII, Step A, using 2-phenyl-2-(N-propylamino)ethanol (Compound 55), to give the expected compound in the form of yellow crystals.

Melting point: 82° C.

Yield: 75%

Step B

N'-benzoyl-N-[α-(2-tetrahydropyranyloxymethyl)benzyl]-N-propylthiourea 1.64 g of para-toluenesulphonic acid are added with stirring, at 0° C., to a solution containing 59.13 g of the N'-benzoylthiourea obtained in the above step in 800 ml of methylene chloride and 78 ml of 2,3-dihydropyran. The reaction medium is left stirring for 2 hours between 0° C. and 30° C. The medium is then washed twice with 500 ml of sodium chloride and sodium bicarbonate solution, and then with saturated aqueous sodium chloride solution.

After evaporation to dryness, the product thus obtained is used in the following step.

Step C 500 ml of 1N sodium hydroxide are added to a solution of 73 g of the protected N'-benzoylthiourea obtained in the above step in 1 litre of ethanol. The reaction medium is maintained at 80° C. for 16 hours and the ethanol is then evaporated off under reduced pressure. Saturated aqueous sodium chloride is added to the alkaline aqueous phase thus obtained and the mixture is extracted with methylene chloride. The organic phase is washed with saturated aqueous sodium chloride, dried over anhydrous sodium sulphate and evaporated to dryness. The residue is purified by chromatography on a column of silica, using a mixture of cyclohexane and ethyl acetate (7:1 v/v) and then 2:1 v/v) as eluent.

The N'-debenzoylation of the thiourea is repeated, if necessary, according to the process indicated above.

N-[α-(2-Tetrahydropyranyloxymethyl)benzyl]-N-propylthiourea is thus obtained in the form of a yellow oil.

Yield: 29%

PREPARATION XIX

N-[α-cycloprolyl-4-(hydroxyethyl)benzyl]-N-propylthiourea (Compound 97)

Step A

N'-benzoyl-N-[α-cyclopropyl-4-(tert-butyldimethylsilyloxyethyl)benzyl]-N-propylthiourea This compound was prepared according to the process described in Preparation XVII, Step A, using N-[α-cyclopropyl-4-(tert-butyldimethylsilyloxyethyl)benzyl]-N-propylamine (Compound 59) as amine.

At the end of the reaction, the reaction medium is evaporated to dryness, the residue is taken up in water and the organic product is extracted with ethyl acetate. For the purification, a chromatography on silica is performed, using a mixture of cyclohexane and ethyl acetate (7:1 v/v) as solvent.

Yield: 75%

Step B 8.8 g of the compound obtained in the above step are dissolved in 120 ml of methanol. 4.5 ml of 30% sodium hydroxide are added, followed by heating to reflux for 8 hours. The methanol is evaporated off, water is added and the mixture is extracted with methylene chloride. The product is purified on a column of silica, eluting with methylene chloride. The following compounds are thus obtained:

N-[α-cyclopropyl-4-(tert-butyldimethylsilyloxyethyl)benzyl]-N-propylthiourea: 10.3%

N-[α-cyclopropyl-4-(hydroxyethyl)benzyl]-N-propylthiourea: 17.3%

N'-benzoyl-N-[α-cyclopropyl-4-(tert-butyldimethylsilyloxyethyl)benzyl]-N-propylthiourea: 34.2%

N'-benzoyl-N-[α-cyclopropyl-4-(hydroxyethyl)benzyl]-N-propylthiourea: 36.9%

0.4 g of N-[α-cyclopropyl-4-(tert-butyldimethylsilyloxyethyl)benzyl]-N-propylthiourea is dissolved in 10 ml of tetrahydrofuran. 1 ml of 1M tetrabutylammonium fluoride solution in tetrahydrofuran is added.

The mixture is left stirring for about 3 hours at room temperature. Saturated aqueous sodium chloride is added and the mixture is extracted with methylene chloride. The organic phase is dried over anhydrous sodium sulphate and evaporated to dryness. The product is purified by chromatography on a column of silica, using a mixture of methylene chloride and methanol (95:5 v/v) as eluent, to give N-[α-cyclopropyl-4-(hydroxyethyl)benzyl]-N-propylthiourea.

Proton nuclear magnetic resonance spectrum (solvent $CDCl_3$): 0.5–0.9 ppm, m, 7H; 1.10–1.40 ppm, m, 1H; 1.40–1.70 ppm, m, 2H; 2.81 ppm, t, 2H; 2.8–3.4 ppm, m, 2H; 3.80 ppm, t, 2H; 5.70–6.1 ppm, m, 3H; 7.00–7.50 ppm, dd, 4H.

PREPARATION XX

N-[cyclopropyl-(2-hydroxy-5-pyridyl)methyl]-N-propylthiourea (Compound 59)

Step A

N'-benzoyl-N-[cyclopropyl-(2-hydroxy-5-pyridyl)methyl]-N-propylthiourea

This compound was prepared from 0.21 g of ammonium thiocyanate, 0.32 ml of benzoyl chloride and 0.72 g of Compound 58, according to the process described in Preparation XVII, Step A.

Yield: 81%

Step B

The process is performed as described in Preparation XVII, Step B, using the N'-benzoylthiourea obtained in the above step, to give the expected product.

Yield: 40%

Proton nuclear magnetic resonance spectrum (solvent $CDCl_3$): 0.3–1.3 ppm, m, 8H; 1.40–1.90 ppm, m, 2H; 2.8–3.4 ppm, m, 2H; 4.70 ppm, s, 2H; 5.8–6.3 ppm, m, 3H; 7.22 ppm, dd, 1H; 7.75 ppm, d, 1H; 8.64 ppm, d, 1H.

PREPARATION XXI

N-(cyclopentyl-4-pyridymethyl)-N-propylthiourea (Compound 99)

Step A

N'-benzoyl-N-(cyclopentyl-4-pyridylmethyl)-N-propylthiourea

This compound is prepared from N-(cyclopentyl-4-pyridylmethyl)-N-propylamine (Compound 37) according to the process described in Preparation XVII, Step A, followed by hydrolysis of the acidic medium for Step B.

6 ml of 32% hydrochloric acid are added to 1.18 g of the compound obtained in Step A. The reaction medium is maintained at 80° C. for 1 hour, then cooled and water is added. The mixture is extracted with methylene chloride and the organic phase is discarded. The aqueous phase is basified with sodium carbonate and extracted with methylene chloride. The organic phase is dried and evaporated under vacuum. The residue is purified by chromatography on a column of silica, using a mixture of methylene chloride and methanol (98:2 v/v) as eluent.

Oil

Yield: 98%

EXAMPLES

Example 1

4-(2,4-dichlorophenyl)-5-ethyl-2-[N-(α-cyclopropyl-4-carboxybenzyl)-N-propylamino]thiazole Step A

4-(2,4-dichlorophenyl)-5-methyl-2-[N-(α-cyclopropyl-4-bromobenzyl)-N-propylamino]thiazole 14 g of 2-bromo-1-(2,4-dichlorophenyl)-1-propanone (Compound 1), 17.1 g of N-(α-cyclopropyl-4-bromobenzyl)-N-propylthiourea (Compound 64) and 7.6 ml of triethylamine are dissolved in 200 ml of ethanol and the solution is heated to 65° C. The reaction is monitored by TLC. At the end of the reaction, the ethanol is removed and the residue is hydrolysed with water and extracted with methylene chloride. The organic phases are washed and dried. The product is purified on a column of silica, using a mixture of cyclohexane and ethyl acetate (20:1 v/v) as eluent.

Yield: 92%

Proton nuclear magnetic resonance spectrum (solvent $CDCl_3$): 0.3–1.0 ppm, m, 7H; 1.2–1.8 ppm, m, 3H; 2.15 ppm, s, 3H; 3.20 ppm, m, 2H; 4.67 ppm, d, 1H; 7.1–7.7 ppm, m, 7H.

Step B 1.8 ml of 1.7N tert-butyllithium in pentane are added dropwise, at −70° C., to 1.59 g of the compound obtained in the above step dissolved in 40 ml of ethyl ether. Once the addition is complete, carbon dioxide is introduced at −70° C., and the temperature is allowed to climb gradually to room temperature. After hydrolysing the reaction medium at 0° C. with ammonium chloride, the mixture is extracted with ethyl acetate. The organic phase is washed with water and then with saturated aqueous sodium chloride solution, dried over anhydrous sodium sulphate and then concentrated under vacuum. The residue is purified on a column of silica, using a mixture of methylene chloride and methanol (85:15 v/v) as eluent, to give 4-(2,4-dichlorophenyl)-5-methyl-2-[N-(α-propyl-4-carboxybenzyl)-N-propylamino]thiazole (white crystals).

Yield: 80%

Melting point: 86° C.

The proton nuclear magnetic resonance spectrum is indicated in Table V.

Example 2

4-(2,4-dichlorophenyl)-5-methyl-2-{N-[αcyclopropyl-4-(methoxycarbonyl)benzyl]-N-propylamino}thiazole 200 mg of thionyl chloride are added to 390 mg of the compound of Example 1 dissolved in 100 ml of anhydrous methanol and the solution is then maintained at 40° C. under argon for 16 hours. After evaporation under vacuum, the residue is purified on a column of silica, using a mixture of cyclohexane and ethyl acetate (10:1 v/v) as eluent. 4-(2,4-Dichlorophenyl)-5-methyl-2-{N-[α-cyclopropyl-4-(methoxycarbonyl)benzyl]-N-propylamino}thiazole is thus obtained.

Yield: 79%

Melting point: gum

The proton nuclear magnetic resonance spectrum is indicated in Table V.

Example 3

4-(2,4-dichlorophenyl)-5-methyl-2-{N-[α-cyclopropyl-4-(ethoxycarbonyl)benzyl]N-propylamino}thiazole This compound was prepared according to the process described in Example 2, but using 100 ml of anhydrous ethanol instead of methanol.

Melting point: gum

The proton nuclear magnetic resonance spectrum is indicated in Table V.

Example 4

4-(2,4-dichlorophenyl)-5-methyl-2-{N-[α-cyclopropyl-4-(hydroxymethyl)benzyl]N-propylamino}thiazole 2 ml of 1N borane solution in tetrahydrofuran are added, at −7° C., to 403 mg of the compound of Example 1 in 15 ml of anhydrous tetrahyrofuran, and the mixture is then left stirring overnight. 10 ml of water and 2 ml of methanol are then added in the presence of potassium carbonate. The reaction mixture is evaporated to dryness under vacuum.

The residue is taken up in 20 ml of ethyl ether and washed with saturated aqueous sodium chloride, dried over anhydrous sodium sulphate and then concentrated under vacuum.

The product is purified on a column of silica, using a mixture of cyclohexane and ethyl acetate (2:1 v/v) as eluent, to give the expected product.

Yield: 94%

Melting point: gum

The proton nuclear magnetic resonance spectrum is indicated in Table V.

Example 5

4-(2,4-dichlorophenyl)-5-methyl-2-{N-[α-cyclopropyl-4-(acetoxymethyl)benzyl]N-propylamino}thiazole 0.6 ml of acetic anhydride and 4-dimethylaminopyridine as catalyst are added, in the presence of 0.3 ml of triethylamine, to 930 g of the compound of Example 4 dissolved in 50 ml of methylene chloride. After stirring for 1 hour at room temperature, a large excess of methanol is added and the reaction medium is then evaporated under vacuum.

The residue is taken up in saturated aqueous sodium chloride and then evaporated under vacuum.

The product is purified on a column of silica, using a mixture of cyclohexane and ethyl acetate (7:1 v/v) as eluent, to give the expected product in the form of an oil.

The proton nuclear magnetic resonance spectrum is indicated in Table V.

4-(2,4-Dichlorophenyl)-5-methyl-2-{N-[α-cyclopropyl-4-(acetoxymethyl)benzyl]-N-propylamino}thiazole hydrochloride is obtained using 0.1N hydrochloric acid solution in isopropanol (white crystals).

Melting point: 54° C.

Example 6

4-(2,4-dichlorophenyl)-5-methyl-2-{N-[α-cyclopropyl-4-(iodmethyl)benzyl]N-propylamino}thiazole 0.35 g of imidazole, 1.32 g of iodine and then 1.6 g of the product of Example 4 are added, at room temperature, to 1.36 g of triphenylphosphine in 50 ml of methylene chloride.

After stirring for 3 hours at room temperature, the reaction medium is washed with water, dried over anhydrous sodium sulphate and then concentrated under vacuum. The residue is taken up in ethyl ether. The triphenylphosphine oxide precipitate is removed by filtration.

The filtrate is purified in the form of an oily residue on a column of silica, using a mixture of cyclohexane and ethyl acetate (20:1 v/v) as eluent, to give the expected product.

Yield: 76%

Melting point: gum

The proton nuclear magnetic resonance spectrum is indicated in Table V.

Example 7

4-(2,4-dichlorophenyl)-5-methyl-2-{N-[α-cyclopropyl-4-(benzyloxyethyl)benzyl]N-propylamino}thiazole 43 mg of sodium hydride are added to 635 mg of the compound of Example 4 dissolved in 80 ml of tetrahydrofuran, followed by 308 mg of benzyl bromide and 665 mg of tetrabutylammonium iodide.

After 48 hours at room temperature, the mixture is extracted with methylene chloride and the organic phase is washed with saturated aqueous sodium chloride, dried over anhydrous sodium sulphate and evaporated under vacuum.

The product is purified on a column of silica, using a mixture of ethyl acetate and cyclohexane (1:20 v/v) as eluent, to give the expected compound.

Yield: 99%

Melting point: gum

The proton nuclear magnetic resonance spectrum of 4-(2,4-dichlorophenyl)-5-methyl-2-{N-[α-cyclopropyl-4-(benzyloxymethyl)benzyl]N-propylamino}thiazole is indicated in Table V.

Example 8

4-(2,4-dichlorophenyl)-5-methyl-2-{N-[α-cyclopropyl-4-(1-hydroxy-1-ethyl)benzyl]N-propylamino}thiazole 4.7 ml of a 1.5M solution of tert-butyllithium in pentane are added dropwise to 1.8 g of the bromo derivative described in Step A of Example 1 dissolved in 40 ml of anhydrous ethyl ether, cooled to −70° C. The temperature is allowed to climb to −50° C., followed by very slow addition, at −70° C., of 0.4 ml of acetaldehyde.

The mixture is left for one hour at −70° C. and is then allowed to warm to a temperature of 0° C. After hydrolysis with 1N hydrochloric acid solution, the ether phase is washed with saturated aqueous sodium chloride and dried over anhydrous sodium sulphate and the product is then purified on a column of silica, using a mixture of cyclohexane and ethyl acetate (3:1 v/v) as eluent.

The expected product is thus obtained in the form of an oil.

Yield: 66%

The proton nuclear magnetic resonance spectrum is indicated in Table V.

4-(2,4-Dichlorophenyl)-5-methyl-2-{N-[α-cyclopropyl-4-(1-hydroxy-1-ethyl)benzyl]N-propylamino}thiazole hydrochloride is obtained by addition of hydrochloric acid dissolved in isopropanol.

Melting point: 85° C.

Example 9

4-(2,4-dichlorophenyl)-5-methyl-2-{N-[α-cyclopropyl-4-(2-hydroxy-2-propanyl)benzyl]N-propylamino}thiazole This compound was obtained according to the process described in Example 8, but using acetone instead of acetaldehyde.

Melting point: gum

The proton nuclear magnetic resonance spectrum of 4-(2,4-dichlorophenyl)-5-methyl-2-{N-[α-cyclopropyl-4-(2-hydroxy-2-propanyl)benzyl]N-propylamino}thiazole is indicated in Table V.

Example 10

4-(2,4-dichlorophenyl)-5-methyl-2-{N-[α-cyclopropyl-4-(1-hydroxy-1-propanyl)benzyl]N-propylamino}thiazole This compound was obtained according to the process described in Example 8, using propionaldehyde as the aldehyde.

Melting point: gum

The proton nuclear magnetic resonance spectrum is indicated in Table V.

Example 11

4-(2,4-dichlorophenyl)-5-methyl-2-{N-[α-cyclopropyl-4-(sulfoxymethyl)benzyl]N-propylanino}thiazole, sodium salt 0.14 ml of distilled pyridine is added to 670 mg of the compound of Example 4 dissolved in 7 ml of anhydrous dimethylformamide, followed, at 0° C., by dropwise addition of 0.12 ml of chlorosulphonic acid in 0.6 ml of methylene chloride.

After stirring for 3 hours at room temperature, the reaction medium is hydrolysed and extracted with methylene chloride, and the organic phase is then dried over anhydrous sodium sulphate and evaporated to dryness.

The residue is taken up in 5 ml of methylene chloride and 1.1 ml of 1.32M sodium methoxide solution are added thereto. The pH is brought to 1 by addition of carboxylic resin.

After filtration, the organic phase gives a precipitate on addition of isopropyl ether.

The expected salt is thus obtained.

Yield: 60%

Melting point: 100° C.–104° C.

The proton nuclear magnetic resonance spectrum is indicated in Table V.

Example 12

4-(2,4-dichlorophenyl)-5-methyl-2-{N-{α-cyclopropyl-4-{3-[(1-methyl-4-piperazinyl)methyl]benzoyloxymethyl}benzyl}-N-propylamino}thiazole Step A 4-(2,4-dichlorophenyl)-5-methyl-2-{N-{α-cyclopropyl-4-[3-(chloromethyl)benzoyloxymethyl]benzyl}-N-propylamino}thiazole 0.6 ml of 3-chloromethylbenzoyl chloride is added dropwise, at 0° C., to 1.6 g of the compound of Example 4 dissolved in 10 ml of anhydrous pyridine. After 2 hours at 0° C., methanol is added to hydrolyze the excess acid chloride and the organic phase is diluted with methylene chloride. This is then washed with 2N hydrochloric acid, with saturated aqueous sodium bicarbonate and then with saturated aqueous sodium chloride and dried over anhydrous sodium sulphate. The organic solvent is evaporated off and the product is purified on a column of silica, using a mixture of cyclohexane and ethyl acetate (20:1 v/v) as eluent, to give the expected product.

Yield: 81%

Step B 0.46 g of potassium carbonate and 0.74 ml of 1-methylpiperazine are added to 0.82 g of the product obtained in the above step dissolved in 5 ml of dimethylformaide. The reaction medium is maintained at 70° C. for 1 hour, followed by hydrolysis and extraction with ethyl acetate.

The organic phase is washed with saturated aqueous sodium chloride and dried over anhydrous sodium sulphate and the residue obtained is purified on a column of silica, using a mixture of methylene chloride and methanol (97:3 v/v) as eluent.

The expected product is thus obtained in the form of an oil.

Yield: 50%

The proton nuclear magnetic resonance spectrum is indicated in Table V.

The corresponding hydrochloride was obtained after addition of a suitable amount of hydrochloric acid dissolved in isopropanol.

Melting point: 166° C.–169° C.

Example 13

4-(2,4-dichlorophenyl)-5-methyl-2-[N-(1-cyclopropyl-2-methoxy-1-ethyl)-N-propylamino]thiazole The process is performed as described in Example 1, Step A, using N-(1-cyclopropyl-2-methoxy-1-ethyl)-N-propylthiourea (Compound 75) as the thiourea, to give the expected compound (gum).

Yield: 48%

The proton nuclear magnetic resonance spectrum is indicated in Table V.

The corresponding hydrochloride was obtained after addition or a suitable amount of hydrochloric acid dissolved in isopropanol and precipitation with isopropyl ether.

Melting point: 154° C.

Example 14

4-(2,4-dichlorophenyl)-5-methyl-2-[N-(α-hydroxymethylbenzyl)-N-propylamino]thiazole Step A 4-(2,4-dichlorophenyl)-5-methyl-2-[N-[α-(2-tetrahydropyranyloxymethyl)benzyl]-N-propylamino}thiazole The process is performed as described in Example 1, Step A, using N-[α-(2-tetrahydropyranyloxymethyl)benzyl]-N-propylthiourea (Compound 96) as the thiourea, to give the expected product (yellow gum).

Yield: 80%

Proton nuclear magnetic resonance spectrum (solvent CDCl$_3$): 0.78 ppm, m, 3H; 1.42–1.75 ppm, m, 8H; 2.16 ppm, s, 3H; 3.20 ppm, m, 2H; 3.5 ppm, m, 1H; 3.82 ppm, m, 1H; 4.0 ppm, m, 1H; 4.3 ppm, m, 1H; 4.72 ppm, d, 1H; 5.5 ppm, m, 1H; 7.22–7.45 ppm, m, 8H.

Step B 19.8 g of the product obtained in the above step are dissolved in 400 ml of a mixture of acetic acid, tetrahydrofuran and water (4:2:1 v/v). The reaction mixture is stirred for 20 hours at 50° C. and then for 4 hours at 70° C. The solvent is evaporated off under reduced pressure and the residue is taken up in 200 ml of 1N sodium hydroxide. The mixture is stirred for 30 minutes and then extracted with methylene chloride. The organic phase is washed with water until neutral and then with saturated aqueous sodium chloride. It is dried over anhydrous sodium sulphate and the residue is purified on a column of silica, using a mixture of cyclohexane and ethyl acetate (7:1 and then 4:1 v/v) as eluent. 4-(2,4-Dichlorophenyl)-5-methyl-2-{N-[α-(hydroxymethyl)benzyl]-N-propylamino}thiazole is thus obtained. Its nuclear magnetic resonance spectrum is indicated in Table V.

Yield: 80%

The corresponding hydrochloride was obtained after addition of a suitable amount of hydrochloric acid dissolved in isopropanol and precipitation with isopropyl ether.

Melting point: 160° C.

Example 15

4-(2,4-dichlorophenyl)-5-methyl-2-{N-[α-(acetoxymethyl)benzyl]-N-propylamino}thiazole 0.28 ml of acetic anhydride is added with stirring, at 0° C., to a solution containing 920 mg of the compound described in Example 14 dissolved in 10 ml of pyridine. The reaction medium is stirred for 14 hours at 20° C., followed by addition of ice and evaporation to dryness. The residue is taken up in toluene and again evaporated to dryness. The residue is dissolved in methylene chloride. The organic phase is washed with water and with saturated aqueous sodium chloride and then dried over anhydrous sodium sulphate and evaporated to dryness. The product is purified on a column of silica using a mixture of cyclohexane and ethyl acetate (9:1 v/v) as eluent, to give the expected product (gum). The proton nuclear magnetic resonance spectrum is indicated in Table V.

Yield: 87%

The product is then salified in the form of the hydrochloride.

Melting point: 54° C.

Example 16

4-(2,4-dichlorophenyl)-5-methyl-2-{N-[α-(methyloxymethyl)benzyl]-N-propylamino}thiazole 0.144 g of sodium hydride is added, with stirring, to a solution of 1.26 g of the product of Example 14 in 15 ml of dimethylformamide. After 2 minutes, 0.56 ml of iodomethane is added to the reaction medium. After stirring for 2 hours between 0° C. and 20° C., ice is added to the reaction medium, followed by extraction with ethyl acetate. The organic phase is washed with water and then with saturated aqueous sodium chloride, dried over anhydrous sodium sulphate and evaporated to dryness. The residue is purified on a chromatography column using a mixture of cyclohexane and ethyl acetate (10:1 v/v) as eluent.

The expected product is thus obtained.

Yield: 93%

4-(2,4-Dichlorophenyl)-5-methyl-2-{N-[α-(methyloxymethyl)benzyl]-N-propylamino}thiazole may be salified in the form of the hydrochloride, which crystallizes in ethyl ether.

Melting point: 154° C. (hydrochloride)

The proton nuclear magnetic resonance spectrum of the base is indicated in Table V.

Example 17

4-(2,4-dichlorophenyl)-5-methyl-2-{N-[α-(ethoxymethyl)benzyl]-N-propylamino}thiazole In order to obtain this coound, the process is performed as described in Example 16, but using iodoethane instead of iodomethane. The proton nuclear magnetic resonance spectrum is indicated in Table V.

Yield: 90%

The corresponding hydrochloride was obtained after addition of a suitable amount of hydrochloric acid solution in isopropanol.

Melting point: 132° C.

Example 18

4-(2,4-dichlorophenyl)-5-methyl-2-{N-[α-(hydroxyethyloxymethyl)benzyl]-N-propylamino}thiazole Step A 1-bromo-2-tetrahydropyran-2-yloxyethane 12 ml of dihydropyran and 20 mg of paratoluenesulphonic acid are added to a solution of 3.7 ml of 2-bromoethanol dissolved in 100 ml of methylene chloride. After stirring for 3 hours at 20° C., the reaction medium is washed with water and then with saturated aqueous sodium chloride, and evaporated to dryness. The residue is distilled at 90° C. at a pressure of 0.5 mbar.

9.9 g of colourless oily %product are obtained.

Yield: 91%

Step B 4-(2,4-dichlorophenyl)-5-methyl-2-{N-[α-(tetrahydropyran-2-yloxyethyloxymethyl)benzyl]-N-propylamino}thiazole A solution containing 1.04 g of the product of Example 14 dissolved in 10 ml of dimethylformamide is cooled to 0° C., followed by addition of 150 mg of sodium hydride as an 80% suspension in oil. 1.05 g of the product obtained in Step A are then added and the mixture is left stirring for about 3 hours. Water is added and the mixture is extracted with ethyl acetate. The extracts are washed with water and evaporated to dryness.

Step C

The residue obtained in Step B is dissolved in a mixture of acetic acid, tetrahydrofuran and water (4:2:1 v/v) and stirred for 3 hours at 70° C. After evaporation to dryness, the residue is taken up in 20 ml of methanol and 20 ml of 1N sodium hydroxide, and stirred at 40° C. for about 10 minutes. The methanol is then evaporated off and the alkaline aqueous phase is extracted with methylene chloride. The organic extract is washed with water and then with saturated aqueous sodium chloride, dried over anhydrous sodium sulphate and evaporated to dryness.

The residue is purified on a column of silica, using a mixture of cyclohexane and ethyl acetate (4:1 v/v) as eluent. The expected product, which may be salified in the form of the hydrochloride, is thus obtained.

Yield: 57%

Melting point: 64° C. (hydrochloride).

The proton nuclear magnetic resonance spectrum of 4-(2,4-dichlorophenyl)-5-methyl-2-{N-[α-(hydroxyethyloxymethyl)benzyl]-N-propylamino}thiazole is indicated in Table V.

Example 19

4-(2,4-dichlorophenyl)-5-methyl-2-{N-[α-(methoxyethyloxymethyl)benzyl]-N-propylamino}thiazole This compound was prepared from the compound described in Example 18 and using the process described in Example 16. The proton nuclear magnetic resonance spectrum is indicated in Table V.

Yield: 70%

The corresponding hydrochloride was obtained after addition of a suitable amount of hydrochloric acid dissolved in isopropanol.

Melting point: 45° C.

Example 20

4-(2,4-dimethyl-5-pyridyl)-5-methyl-2-[N-(dicyclopropylmethyl)-N-propylamino]thiazole This compound was prepared according to the process described in Example 1, Step A, using 2-bromo-1-(2,4-dimethyl-5-pyridyl)-1-propanone (Coapound 27) as the ketone and N-(dicyclopropylmethyl)-N-propylthiourea (Compound 66) as the thiourea.

Yield: 80%

The proton nuclear magnetic resonance spectrum is indicated in Table V.

Examples 21 and 22

The compounds of Examples 21 and 22 were obtained according to the process described in Example 20, using the substituted bromo ketones and suitable thioureas. Their spectral characteristics are indicated in Table V.

Example 23

4-(2,4-dihydroxymethylphenyl)-5-methyl-2-[N-(α-cycloproplybenzyl)-N-propylamino]thiazole Step A 4-(2,4-dicarboxyphenyl)-5-methyl-2-[N-(α-cyclopropylbenzyl)-N-propylamino]thiazole 5 ml of a 1.7M solution of tert-butyllithium in pentane are added, at −70° C., to 1.1 g of 4-(2,4-dibromophenyl)-5-methyl-2-[N-(α-cyclopropylbenzyl)-N-propylamino]thiazole (prepared from 2-bromo-1-(2,4-dibromophenyl)-1-propanone (Compound 14) and N-(α-cyclopropylbenzyl)-N-propylthiourea (Compound 65), according to the process described in Example 1, Step A), dissolved in 30 ml of anhydrous ethyl ether. The temperature is allowed to rise to −50° C. and the mixture is then subjected to the action of carbon dioxide, allowing the temperature to rise to 20° C.

After hydrolysis of the reaction mixture at 0° C. with 1N hydrochloric acid and extraction with ethyl acetate, the organic phase is washed with water, dried over anhydrous sodium sulphate and evaporated to dryness.

The expected product is thus obtained.

Yield: 99%

Step B 1 g of the compound obtained in Step A is dissolved in 20 ml of anhydrous tetrahydrofuran, followed, at −7° C., by addition of 5 ml of 1M borane solution in tetrahydrofuran, and the mixture is stirred overnight. 0.5 g of potassium carbonate and 10 ml of a mixture of methanol and water (1:1 v/v) are then added. The mixture is maintained at 60° C. for 2 hours and then cooled and evaporated under vacuum. The residue is taken up in water and extracted with ethyl ether, and the organic phase is washed with water, then with saturated aqueous sodium chloride and dried over anhydrous sodium sulphate. It is evaporated to dryness and the residue is taken up in pentane. The expected product is thus obtained.

The proton nuclear magnetic resonance spectrum is indicated in Table V.

Yield: 40%

Example 24

4-[2-chloro-4-(1-hydroxy-1-ethyl)-phenyl]-5-methyl-2-[N-(dicyclopropylmethyl)-N-propylamino]thiazole This compound was prepared from 4-(4-bromo-2-chlorophenyl)-5-methyl-2-[N-(dicyclopropylmethyl)-N-propylamino]thiazole, using the preparation process described in Example 8.

The proton nuclear magnetic resonance spectrum is indicated in Table V.

Yield: 83%

4-(4-Bromo-2-chlorophenyl)-5-methyl-2-[N-(dicyclopropylmethyl)-N-propylamino]thiazole was obtained from Compound 16 and from Compound 66 according to the process described in Example 1, Step A.

4-[2-Chloro-4-(1-hydroxy-1-ethyl)phenyl]-5-methyl-2-[N-(dicyclopropylmethyl)-N-propylamino]thiazole hydrochloride was obtained after addition of a suitable amount of hydrochloric acid dissolved in isopropanol.

Melting point: 93° C.

Example 25

4-[4-chloro-2-(1-hydroxy-1-ethyl)phenyl]-5-methyl-2-[N-(dicyclopropylmethyl)-N-propylaina]thiazole This compound was prepared according to the process described in Example 24, from 4-(2-bromo-4-chlorophenyl)-5-methyl-2-[N-(dicyclopropylmethyl)-N-propylamino]thiazole.

The proton nuclear magnetic resonance spectrum is indicated in Table V.

Yield: 83%

The hydrochloride was obtained after addition of a suitable amount of hydrochloric acid dissolved in isopropanol.

Melting point: 123° C.

Example 26

4-(2,4-dichlorophenyl)-5-methyl-2-[N-(α-cyclopropylbenzyl)-N-(2-tetrahydropyranyloxyethyl)amino]-thiazole 4-(2,4-Dichlorophenyl)-5-methyl-2-[N-(α-cyclopropylbenzyl)amino]thiazole was prepared from 2-bromo-1-(2,4-dichlorophenyl)-1-propanone (Compound 1) and N-(α-cyclopropylbenzyl)thiourea (Compound 74) according to the process described in Example 1, Step A. 4 g of this compound is dissolved in 60 ml of anhydrous dimethylformamide and the solution is cooled to 5° C., followed by portionwise addition of 493 mg of sodium hydride. After stirring for one hour at room temperature, 3.14 g of 1-bromo-2-(2- tetrahydropyranyloxy) ethane dissolved in 30 ml of dimethylformamide are added dropwise thereto. The mixture is left stirring for 3 hours. After addition of water and extraction with ethyl acetate, the organic phase is washed with water, dried over anhydrous sodium sulphate and evaporated to dryness. The residue is purified on a column of silica, using a mixture of cyclohexane and ethyl acetate (1:1 v/v) as eluent. The expected product is thus obtained.

The proton nuclear magnetic resonance spectrum is indicated in Table V.

Yield: 99%

The corresponding hydrochloride was obtained after addition of a suitable mount of hydrochloric acid dissolved in isopropanol.

Melting point; 109° C.

Example 27

4-(2,4-dichlorophenyl)-5-methyl-2-[N-(α-cyclopropylbenzyl)-N-(2-hydroxy-1-ethyl)amino]thiazole 4 g of the product of Example 26 are dissolved in a mixture of acetic acid, tetrahydrofuran and water (4:2:1 v/v), and the solution is heated at 40° C. for 18 hours and then evaporated to dryness. The residue is purified on a column of silica, using a mixture of cyclohexane and ethyl acetate as eluent, to give the expected product.

Yield: 90%

Melting point. 128° C.

Example 28 to 31

The compounds of Examples 28 and 31 were obtained according to the process described in Example 1, Step A, using the substituted bromoacetones and suitable thioureas. Their spectral characteristics are indicated in Table V.

Example 32

4-(2,4-dichlorophenyl)-5-methyl-2-{N-[α-(cyclopropylmethoxymethyl)benzyl]-N-propylamino}thiazole 32 mg of sodium hydride are added with stirring, at 0° C., to a solution of 4.64 mg of the compound of Example 14 dissolved in 7 ml of dimethylformamide, followed by addition of 0.19 ml of cyolopropylmethyl bromide. The reaction medium is stirred for 16 hours at room temperature. The medium is then poured onto ice and extracted with ethyl acetate, and the extracts are washed with water and then with saturated aqueous sodium chloride, dried over anhydrous sodium sulphate and evaporated to dryness. The residue is purified by chromatography on a column of silica, using a mixture of cyclohexane and ethyl acetate as eluent. The expected product is thus obtained.

The proton nuclear magnetic resonance spectrum is indicated in Table V.

Yield: 50%

The corresponding hydrochloride was obtained after addition of a suitable amount of hydrochloric acid dissolved in isopropanol.

Melting point: 58° C.

Example 33

4-(2,4-dichlorophenyl)-5-methyl-2-{N-[α-(cyclopropyl)-4-(methyl)benzyl]-N-propylamino}thiazole 0.042 g of sodium hydride is added, at 0° C., to 0.64 g of 2-{N-[α-cyclopropyl-4-(hydroxyethyl)benzyl]-N-propylamino}thiazole (Example 28) in 15 ml of anhydrous dimethylformamide, and the suspension is stirred for 20 minutes. 0.09 ml of methyl iodide is then added and the reaction mixture is left for 3 hours at room temperature. It is then poured onto crushed ice and extracted three times with ethyl acetate. The organic phase is successively washed with water, dried over sodium sulphate and then concentrated under vacuum. The residue obtained is chromatographed on silica gel, eluent: cyclohexane/ethyl acetate (10/1-v/v). The fractions containing pure product are concentrated to give 0.5 g of the expected product, which crystallizes in the form of the hydrochloride.

Yield: 75%

The spectral characteristics of this product are indicated in Table V below.

Examples 34–58

The compounds of Examples 34 to 58 were obtained according to the process described in Example 1, Step A, using the substituted bromo ketones and suitable thioureas. Their spectral characteristics are indicated in Table V.

TABLE V

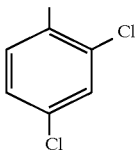

| EX-AMPLE | R₁ | R₂ | R₃ | R₄ | R₅ | NMR SPECTRUM (SOLVENT) |
|---|---|---|---|---|---|---|
| 1 | —CH₃ |  | —C₃H₇ | 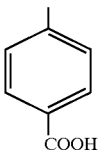 | 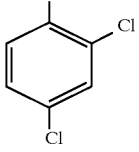 | (DMSO-d₆) acid 0.45–0.84 ppm, m, 7H; 1.6 ppm, m, 3H; 2.09 ppm, s, 3H; 3.3 ppm, m, 2H; 4.50 ppm, d, 1H; 7.4–7.9 ppm, m, 7H; 12.8 ppm, m, 1H. |
| 2 | —CH₃ |  | —C₃H₇ | 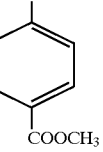 | 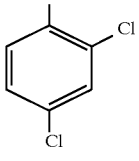 | (CDCl₃) Base 0.3–0.8 ppm, m, 7H; 1.5 ppm, m, 3H; 2.14 ppm, s, 3H; 3.1 ppm, m, 2H; 3.88 ppm, s, 3H; 4.7 ppm, d, 1H; 7.9–8.0 ppm, m, 7H. |
| 3 | —CH₃ |  | —C₃H₇ | 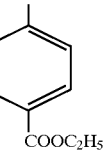 | 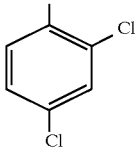 | (CDCl₃) Base 0.42–0.87 ppm, m, 7H; 1.37 ppm, m, 4H; 1.7 ppm, m, 2H; 2.14 ppm, s, 3H; 3.2 ppm, m, 2H; 4.36 ppm, q, 2H; 4.77 ppm, d, 1H; 7.2–7.6 ppm, m, 5H; 7.99 ppm, m, 2H. |
| 4 | —CH₃ |  | —C₃H₇ |  | 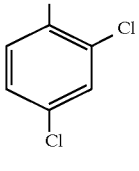 | (CDCl₃) Base 0.25–0.85 ppm, m, 7H; 1.3 ppm, m, 1H; 1.60 ppm, m, 2H; 2.05 ppm, s, 3H; 3.12 ppm, m, 2H; 3.55 ppm, m, 1H; 4.3 ppm, s, 2H; 4.6 ppm, d, 1H; 7.5–7.0 ppm, m, 7H. |
| 5 | —CH₃ |  | —C₃H₇ |  | 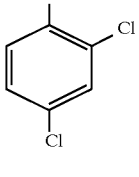 | (CDCl₃) Base 0.4–0.95 ppm, m, 7H; 1.4 ppm, m, 1H; 1.75 ppm, m, 2H; 2.08 ppm, s, 3H; 2.17 ppm, s, 3H; 3.25 ppm, m, 2H; 4.75 ppm, d, 1H; 5.11 ppm, s, 2H; 7.15–7.7 ppm, m, 7H. |
| 6 | —CH₃ |  | —C₃H₇ | 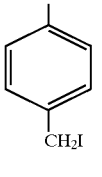 | 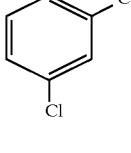 | (CDCl₃) Base 0.4–1.1 ppm, m, 7H; 1.4 ppm, m, 1H; 1.8 ppm, m, 2H; 2.2 ppm, s, 3H; 3.3 ppm, m, 2H; 4.5 ppm, s, 2H; 4.75 ppm, d, 1H; 7.2–7.6 ppm, m, 7H. |
| 7 | —CH₃ |  | —C₃H₇ | 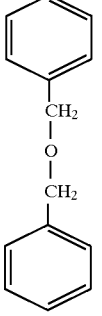 |  | (CDCl₃) Base 0.4–1.0 ppm, m, 7H; 1.4 ppm, m, 1H; 1.8 ppm, m, 2H; 2.20 ppm, s, 3H; 3.25 ppm, m, 2H; 4.6 ppm, s, 4H; 4.75 ppm, s, 1H; 7.2–7.6 ppm, m, 12H. |

TABLE V-continued

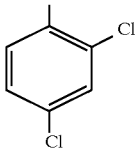

| EX-AMPLE | R₁ | R₂ | R₃ | R₄ | R₅ | NMR SPECTRUM (SOLVENT) |
|---|---|---|---|---|---|---|
| 8 | —CH₃ |  | —C₃H₇ | 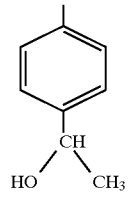 | 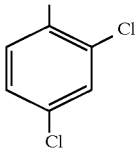 | (CDCl₃) Base 0.70–1.20 ppm, m, 7H; 1.41 ppm, m, 1H; 1.46 ppm, d, 3H; 1.74 ppm, m, 2H; 2.03 ppm, s, 3H; 3.6 ppm, m, 2H; 4.88 ppm, q, 1H; 5.1 ppm, m, 1H; 7.2–7.5 ppm, m, 7H. |
| 9 | —CH₃ |  | —C₃H₇ | 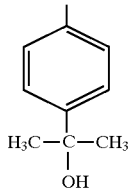 | 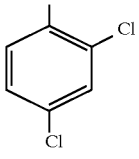 | (CDCl₃) Base 0.4–0.9 ppm, m, 7H; 1.4 ppm, m, 1H; 1.58 ppm, s, 8H; 1.75 ppm, m, 3H; 2.15 ppm, s, 3H; 3.2 ppm, m, 2H; 4.84 ppm, d, 1H; 7.1–7.5 ppm, m, 7H. |
| 10 | —CH₃ |  | —C₃H₇ | 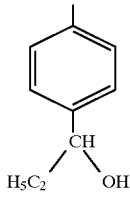 | 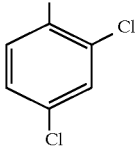 | (CDCl₃) Base 0.5–1.8 ppm, m, 15H; 2.1 ppm, s, 3H; 3.2 ppm, m, 2H; 4.6 ppm, m, 2H; 7.1–7.5 ppm, m, 7H. |
| 11 | —CH₃ |  | —C₃H₇ | 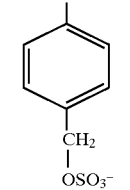 | 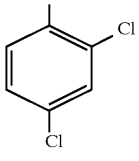 | (CDCl₃) Base 0.2–0.9 ppm, m, 7H; 1.1–1.25 ppm, m, 1H; 1.4–1.8 ppm, m, 2H; 2.07 ppm, s, 3H; 3.0–3.3 ppm, m, 2H; 4.54 ppm, d, 1H; 4.98 ppm, s, 2H; 7.1–7.5 ppm, m, 7H. |
| 12 | —CH₃ |  | —C₃H₇ | 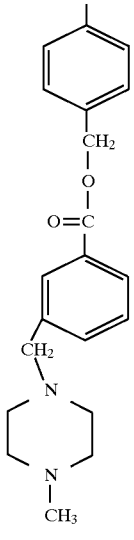 | | (CDCl₃) Base 0.2–0.9 ppm, m, 7H; 1.1–1.8 ppm, m, 3H; 1.9–2.5 ppm, m, 14H; 2.9–3.3 ppm, m, 2H; 3.49 ppm, s, 2H; 4.67 ppm, d, 1H; 5.34 ppm, s, 2H; 7.1–7.6 ppm, m, 9H; 7.7–8.0 ppm, m, 2H. |

TABLE V-continued (I) Structure: R1-C(S-)=C(R2)-N=C(-N(R3)(CH(H)(C(R4)(R5))))

| EX-AMPLE | R₁ | R₂ | R₃ | R₄ | R₅ | NMR SPECTRUM (SOLVENT) |
|---|---|---|---|---|---|---|
| 13 | —CH₃ | 2,4-dichlorophenyl | —C₃H₇ | —CH₂OCH₃ | cyclopropyl | (CDCl₃) Base 0.37–0.46 ppm, m, 4H; 0.93 ppm, m, 3H; 1.15 ppm, m, 1H; 1.79 ppm, m, 2H; 2.12 ppm, s, 3H; 3.31 ppm, s, 3H; 3.30–3.50 ppm, m, 3H; 3.65 ppm, m, 2H; 7.25–7.42 ppm, m, 3H. |
| 14 | —CH₃ | 2,4-dichlorophenyl | —C₃H₇ | —CH₂OH | phenyl | (CDCl₃) Base 0.85 ppm, t, 3H; 1.6 ppm, m, 2H; 2.18 ppm, s, 3H; 3.16 ppm, m, 2H; 4.12 ppm, m, 2H; 5.8 ppm, s, 1H; 5.13 ppm, m, 1H; 7.21–7.45 ppm, m, 8H. |
| 15 | —CH₃ | 2,4-dichlorophenyl | —C₃H₇ | —CH₂OCOCH₃ | phenyl | (CDCl₃) Base 0.76 ppm, t, 3H; 1.5 ppm, m, 2H; 1.99 ppm, s, 3H; 2.16 ppm, s, 3H; 3.1 ppm, m, 2H; 4.68 ppm, d, 2H; 5.70 ppm, t, 1H; 7.23–7.45 ppm, m, 8H. |
| 16 | —CH₃ | 2,4-dichlorophenyl | —C₃H₇ | —CH₂OCH₃ | phenyl | (CDCl₃) Base 0.8 ppm, t, 3H; 1.6 ppm, m, 2H; 2.17 ppm, s, 3H; 3.15 ppm, m, 2H; 3.42 ppm, s, 3H; 3.97 ppm, d, 2H; 5.59 ppm, t, 1H; 7.20–7.47 ppm, m, 8H. |
| 17 | —CH₃ | 2,4-dichlorophenyl | —C₃H₇ | —CH₂OC₂H₅ | phenyl | (CDCl₃) Base 0.78 ppm, t, 3H; 1.18 ppm, t, 3H; 1.50 ppm, m, 2H; 2.15 ppm, s, 3H; 3.17 ppm, m, 2H; 3.55 ppm, q, 2H; 4.0 ppm, d, 2H; 5.54 ppm, t, 1H; 7.26–7.45 ppm, m, 8H. |
| 18 | —CH₃ | 2,4-dichlorophenyl | —C₃H₇ | —CH₂OC₂H₄OH | phenyl | (CDCl₃) Base 1.77 ppm, t, 3H; 1.55 ppm, m, 2H; 2.16 ppm, s, 3H; 3.11 ppm, m, 2H; 3.64 ppm, s, 4H; 4.08 ppm, m, 2H; 5.65 ppm, t, 1H; 7.20–7.46 ppm, m, 8H. |
| 19 | —CH₃ | 2,4-dichlorophenyl | —C₃H₇ | —CH₂OC₂H₄OCH₃ | phenyl | (CDCl₃) Base 0.77 ppm, t, 3H; 1.60 ppm, m, 2H; 2.16 ppm, s, 3H; 3.13 ppm, m, 2H; 3.35 ppm, s, 3H; 3.45–3.70 ppm, m, 4H; 4.07 ppm, d, 2H; 5.57 ppm, t, 1H; 7.20–7.45 ppm, m, 8H. |
| 20 | —CH₃ | 2,6-dimethylpyridin-4-yl | —C₃H₇ | cyclopropyl | cyclopropyl | (CDCl₃) Base 0.3–0.8 ppm, m, 7H; 0.9–1.2 ppm, m, 6H; 1.87 ppm, m, 2H; 2.08 ppm, s, 3H; 2.54 ppm, s, 3H; 2.83 ppm, s, 3H; 3.60 ppm, m, 2H; 4.0 ppm, m, 1H; 7.5 ppm, m, 1H; 8.4 ppm, m, 1H. |

TABLE V-continued (I) structure: R1,R2 on C=C with S connecting to C(=N)-N(R3)-CH(R4)(R5)

| EX-AMPLE | R₁ | R₂ | R₃ | R₄ | R₅ | NMR SPECTRUM (SOLVENT) |
|---|---|---|---|---|---|---|
| 21 | —CH₃ | 2,6-dichloropyridin-3-yl | —C₃H₇ | cyclopropyl | phenyl | (CDCl₃) Base 0.3–0.9 ppm, m, 7H; 1.2–1.8 ppm, m, 3H; 2.19 ppm, s, 3H; 3.2 ppm, m, 2H; 4.50 ppm, d, 1H; 6.9–7.7 ppm, m, 7H. |
| 22 | —CH₃ | 2,6-dichloropyridin-3-yl | —C₃H₇ | cyclopropyl | cyclopropyl | (CDCl₃) Base 0.3–1.2 ppm, m, 13H; 1.5–2.0 ppm, m, 2H; 2.1 ppm, s, 3H; 3.6 ppm, m, 3H; 7.25 ppm, d, 1H; 7.8 ppm, d, 1H. |
| 23 | —CH₃ | 2,6-bis(hydroxymethyl)phenyl | —C₃H₇ | cyclopropyl | phenyl | (CDCl₃) Base 0.4–0.9 ppm, m, 7H; 1.2–1.9 ppm, m, 4H; 2.27 ppm, s, 3H; 3.24 ppm, m, 2H; 4.25 ppm, d, 1H; 4.44 ppm, s, 2H; 4.57 ppm, m, 1H; 4.64 ppm, s, 2H; 7.2–7.5 ppm, m, 8H. |
| 24 | —CH₃ | 3-chloro-4-(1-hydroxyethyl)phenyl | —C₃H₇ | cyclopropyl | cyclopropyl | (CDCl₃) Base 0.3–0.7 ppm, m, 7H; 0.8–1.35 ppm, m, 6H; 1.38 ppm, d, 3H; 1.8 ppm, m, 2H; 2.15 ppm, s, 3H; 3.24 ppm, t, 1H; 3.4 ppm, m, 2H; 4.0 ppm, m, 1H; 4.68 ppm, q, 1H; 7.0–7.4 ppm, m, 3H. |
| 25 | —CH₃ | 5-chloro-2-(1-hydroxyethyl)phenyl | —C₃H₇ | cyclopropyl | cyclopropyl | (CDCl₃) Base 0.35–0.6 ppm, m, 8H; 0.8–1.5 ppm, m, 8H; 1.8 ppm, m, 2H; 2.2 ppm, s, 3H; 2.79 ppm, t, 1H; 3.3 ppm, m, 2H; 4.70 ppm, q, 1H; 6.0 ppm, m, 1H; 7.2–7.4 ppm, m, 3H. |
| 26 | —CH₃ | 2,4-dichlorophenyl | —(CH₂)₂—O—(tetrahydropyran-2-yl) | cyclopropyl | phenyl | (CDCl₃) Base 0.4–0.9 ppm, m, 4H; 1.5 ppm, m, 7H; 2.13 ppm, s, 3H; 3.3–4.0 ppm, m, 6H; 4.5 ppm, m, 2H; 7.1–7.6 ppm, m, 8H. |
| 27 | —CH₃ | 2,4-dichlorophenyl | —CH₂CH₂OH | cyclopropyl | phenyl | (CDCl₃) Base 0.4–0.9 ppm, m, 4H; 1.45 ppm, m, 1H; 2.10 ppm, s, 3H; 3.4–3.9 ppm, m, 5H; 7.1–7.5 ppm, m, 8H. |

TABLE V-continued

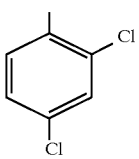 (I)

| EX-AMPLE | R₁ | R₂ | R₃ | R₄ | R₅ | NMR SPECTRUM (SOLVENT) |
|---|---|---|---|---|---|---|
| 28 | —CH₃ |  | —C₃H₇ | 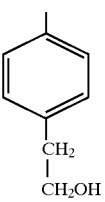 | 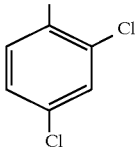 | (CDCl₃) Base 0.4–0.9 ppm, m, 7H; 1.25–1.35 ppm, m, 1H; 1.6–1.8 ppm, m, 2H; 2.15 ppm, s, 3H; 2.82 ppm, t, 2H 3.1–3.3 ppm, m 2H; 3.80 ppm, t, 2H; 4.62 ppm, d, 1H; 7.1–7.4 ppm, m, 7H. |
| 29 | —CH₃ |  | —C₃H₇ | 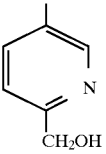 | 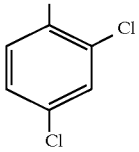 | (CDCl₃) Base 0.3–1.0 ppm, m, 7H; 1.1–1.9 ppm, m, 3H; 2.13 ppm, s, 3H; 2.6–2.8 ppm, m, 3H; 4.7–4.8 ppm, m, 3H; 7.1–7.3 ppm, m, 4H; 7.76 ppm, dd, 1H; 8.69 ppm, d, 1H. |
| 30 | —CH₃ | 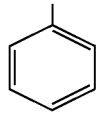 | —C₃H₇ | —CH₂CH₂OCH₃ | 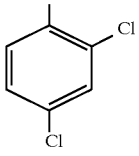 | (CDCl₃) Base 0.75 ppm, m, 3H; 1.49 ppm, m, 2H; 2.17 ppm, s, 3H; 2.31 ppm, m, 2H; 3.08 ppm, m, 2H; 3.32 ppm, s, 3H; 3.50 ppm, m, 2H; 5.48 ppm, t, 1H; 7.20–7.47 ppm, s, 8H. |
| 31 | —CH₃ | 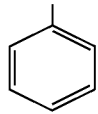 | —C₃H₇ | —CH₂SCH₃ | 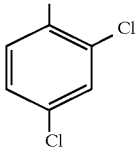 | (CDCl₃) Base 0.75 ppm, m, 3H; 1.44 ppm, m, 2H; 2.17 ppm, s, 6H; 3.07 ppm, m, 2H; 3.20 ppm, d, 2H; 5.64 ppm, t, 1H; 7.22–7.48 ppm, m, 8H. |
| 32 | —CH₃ |  | —C₃H₇ | —CH₂OCH₂—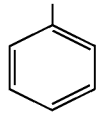 | 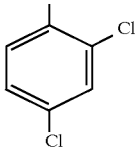 | (CDCl₃) Base 0.2–0.55 ppm, m, 4H; 0.82 ppm, m, 3H; 1.0 ppm, m, 1H; 1.5 ppm, m, 2H; 2.18 ppm, s, 3H; 3.22 ppm, m, 2H; 3.40 ppm, d, 2H; 4.08 ppm, d, 2H; 5.60 ppm, t, 1H; 7.20–7.48 ppm, m, 8H. |
| 33 | —CH₃ |  | —C₃H₇ | 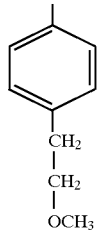 | 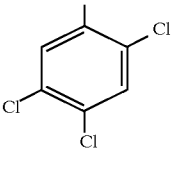 | (CDCl₃) Base 0.5–0.9 ppm, m, 7H; 1.5–1.8 ppm, m, 2H; 2.15 ppm, s, 3H; 2.87 ppm, t, J = 7 Hz, 2H; 3.18 ppm, m, 2H 3.35 ppm, s 3H; 3.6 ppm, t, J = 7 Hz, 2H; 4.6 ppm, d, J = 10 Hz, 1H; 7.1–7.4 ppm, m, 7H. |
| 34 | —CH₃ | 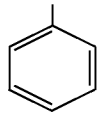 | —C₃H₇ | —CH₂OCH₃ | 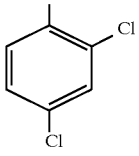 | (CDCl₃) Base 0.85 ppm, m, 3H; 1.4–1.8 ppm, m, 2H; 2.2 ppm, s, 3H; 3.22 ppm, m, 2H; 3.47 ppm, s, 3H 4 ppm, d J = 6.5 Hz, 2H; 5.6 ppm, t, J = 6.5 Hz, 7.3–7.7 ppm, m, 7H. |

TABLE V-continued

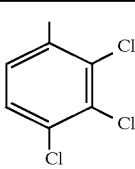

| EX-AMPLE | R₁ | R₂ | R₃ | R₄ | R₅ | NMR SPECTRUM (SOLVENT) |
|---|---|---|---|---|---|---|
| 35 | —CH₃ | 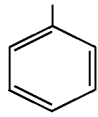 | —C₃H₇ | —CH₂OCH₃ | 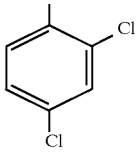 | (CDCl₃) Base 0.82 ppm, m, 3H; 1.4–1.8 ppm, m, 2H; 2.2 ppm, s, 3H; 3.25 ppm, m, 2H; 3.45 ppm, s, 3H 4 ppm, d J = 8.4 Hz, 2H; 5.65 ppm, t, J = 6.4 Hz, 1H; 7.2–7.6 ppm, m, 7H. |
| 36 | —CH₃ |  | —C₃H₇ | 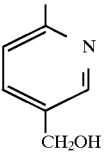 | 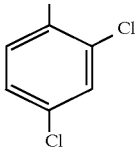 | (CDCl₃) Base 0.2–0.9 ppm, m, 7H; 1.4–1.7 ppm, m, 3H; 2.1 ppm, s, 3H; 2.3 ppm, m, 1H; 3.3 ppm, m, 2H 4.65 ppm, d + s, 3H; 7.2–7.6 ppm, m, 5H; 8.48 ppm, s, 1H. |
| 37 | —CH₃ | 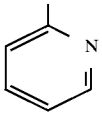 | —C₃H₇ | —CH₂OCH₃ | 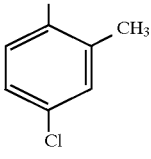 | (CDCl₃) Base 0.83 ppm, m, 3H; 1.41–1.61 ppm, m, 2H; 2.13 ppm, s, 3H; 3.21–3.31 ppm, m, 2H; 4.08–4.15 ppm, m, 2H 5.68 ppm, m 1H; 7.12–7.42 ppm, m, 5H; 7.59 ppm, m, 1H; 8.52 ppm, m, 1H. |
| 38 | —CH₃ | 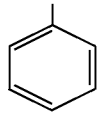 | —C₃H₇ | —CH₂OCH₃ | 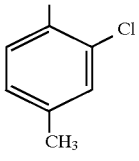 | (CDCl₃) Base 0.81 ppm, m, 3H; 1.45–1.64 ppm, m, 2H; 2.18 ppm, s, 3H; 2.28 ppm, s, 3H; 3.14–3.24 ppm, m, 2H 3.42 ppm, s 3H; 3.98 ppm, d, J = 6.4 Hz, 2H; 5.58 ppm, t, J = 6.4 Hz, 7.19–7.41 ppm, m, 8H. |
| 39 | —CH₃ | 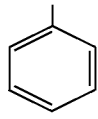 | —C₃H₇ | —CH₂OCH₃ | 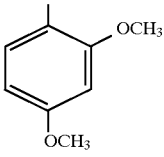 | (CDCl₃) Base 0.80 ppm, m, 3H; 1.44–1.63 ppm, m, 2H; 2.18 ppm, m, 3H; 2.35 ppm, s, 3H; 3.10–3.20 ppm, m, 2H 3.42 ppm, s, 3H; 3.98 ppm, d, J = 6.4 Hz, 2H; 5.62 ppm, t, J = 6.4 Hz, 1H; 7.08 ppm, d, J = 8 Hz, 1H; 7.24–7.44 ppm, m, 7H. |
| 40 | —CH₃ | 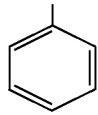 | —C₃H₇ | —CH₂OCH₃ | 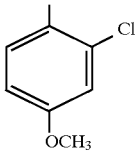 | (CDCl₃) Base 0.80 ppm, m, 3H; 1.44–1.63 ppm, m, 2H; 2.17 ppm, s, 3H; 3.16 ppm, m, 2H; 3.43 ppm, s, 3H 3.81 ppm, s 3H; 3.84 ppm, s, 3H; 3.98 ppm, d, J = 6.5 Hz, 2H; 5.64 ppm, t, J = 8.5 Hz, 1H, 6.53 ppm, s, 1H; 6.57, d, J = 8 Hz, 1H; 7.25–7.45 ppm, m, 8H. |
| 41 | —CH₃ | 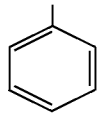 | —C₃H₇ | —CH₂OCH₃ | 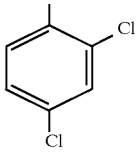 | (CDCl₃) Base 0.78 ppm, m, 3H; 1.50–1.62 ppm, m, 2H; 2.17 ppm, s, 3H; 3.09–3.15 ppm, m, 2H; 3.42 ppm, s, 3H 3.80 ppm, s 3H; 3.98 ppm, d, J = 6.4 Hz, 2H; 5.61 ppm, t, J = 6.4 Hz, 1H; 6.83 ppm, dd, J1 = 2.6 Hz, J2 = 8.6 Hz, 1H; 6.99, d, J = 2.6 Hz, 1H; 7.25–7.42 ppm, m, 6H. |

TABLE V-continued

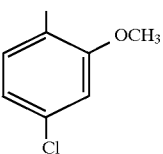

(I)

| EX-AMPLE | R₁ | R₂ | R₃ | R₄ | R₅ | NMR SPECTRUM (SOLVENT) |
|---|---|---|---|---|---|---|
| 42 | —CH₃ | 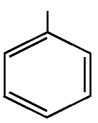 | —C₃H₇ | —CH₂OCH₃ | 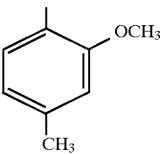 | (CDCl₃) Base<br>0.80 ppm, m, 3H; 1.51–1.63 ppm, m, 2H; 2.16 ppm, d, 3H; 3.10–3.20 ppm, m, 2H; 3.42 ppm, s, 3H 3.82 ppm, s 3H; 3.98 ppm, d, J = 6.5 Hz, 2H; 5.61 ppm, t, J = 6.5 Hz, 1H; 6.94 ppm, d, J = 1.8 Hz, 1H; 6.99 ppm, dd, J1 = 1.8 Hz, J2 = 8 Hz, 1H; 7.24–7.43 ppm, m, 6H. |
| 43 | —CH₃ | 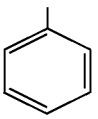 | —C₃H₇ | —CH₂OCH₃ | 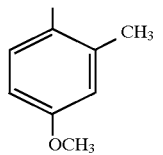 | (CDCl₃) Base<br>0.82 ppm, m, 3H; 1.46–1.66 ppm, m, 2H; 2.21 ppm, s, 3H; 2.41 ppm, s, 3H; 3.12–3.23 ppm, m, 2H 3.44 ppm, s 3H; 3.84 ppm, s, 3H; 4.01 ppm, d, J = 6.5 Hz, 2H; 5.67 ppm, t, J = 6.5 Hz, 1H; 6.80 ppm; s, 1H; 6.85 ppm, d, J = 7.8 Hz, 1H; 7.28–7.46 ppm, m, 6H. |
| 44 | —CH₃ | 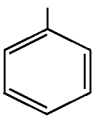 | —C₃H₇ | —CH₂OCH₃ | 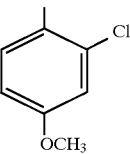 | (CDCl₃) Base<br>0.81 ppm, m, 3H; 1.52–1.65 ppm, m, 2H; 2.18 ppm, s, 3H; 2.29 ppm, s, 3H; 3.12–3.23 ppm, m, 2H 3.43 ppm, s 3H; 3.82 ppm, s, 3H; 3.98 ppm, d, J + 6.4 hz, 2H; 5.61 ppm, t, J = 6.4 Hz, 1H; 6.75–6.82 ppm, m, 2H; 7.20–7.42 ppm, m, 6H. |
| 45 | —CH₃ |  | —C₃H₇ | —CH₂OCH₃ | 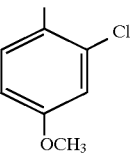 | (CDCl₃) Base<br>0.35–0.60 ppm, m, 4H; 0.93 ppm, m, 3H; 1.15 ppm, m, 1H; 1.70 ppm, m, 2H; 2.12 ppm, s, 3H 3.32 ppm, s 3H; 3.31–3.35 ppm, m, 2H; 3.47 ppm, m, 1H; 3.65 ppm, m, 2H; 3.79 ppm, s, 3H; 6.80 ppm, dd, J1 = 2.6 Hz, J2 = 8.5 Hz, 1H; 6.95 ppm, d, J = 2.6 Hz, 1H; 7.27 ppm, d, J = 8.5 Hz, 1H. |
| 46 | —CH₃ | 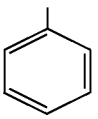 | —C₃H₇ | —CH₂SCH₃ | 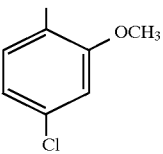 | (CDCl₃) Base<br>0.73 ppm, m, 3H; 1.40–1.65 ppm, m, 2H; 2.17 ppm, 2s, 6H; 3.01–3.09 ppm, m, 2H; 3.19 ppm, d, J = 7.6 Hz, 2H 3.81 ppm, s 3H; 5.84 ppm, t, J = 7.6 Hz, 1H; 6.84 ppm, dd, J1 = 2.6 Hz, J2 = 8.4 Hz, 1H; 6.69 ppm, d, J = 2.6 Hz, 1H; 7.30–7.44 ppm, m, 6H. |
| 47 | —CH₃ | 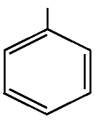 | —C₃H₇ | —CH₂SCH₃ | 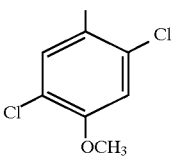 | (CDCl₃) Base<br>0.75 ppm, m, 3H; 1.40–1.60 ppm, m, 2H; 2.17 ppm, s, 3H; 2.19 ppm, s, 3H; 3.02–3.10 ppm, m, 2H 3.20 ppm, d J = 7.7 Hz, 2H; 3.83 ppm, s, 3H; 5.64 ppm, t, J = 7.7 Hz, 2H; 3.83 ppm, s, 3H; 5.64 ppm, t, J = 7.7 Hz, 1H; 6.95 ppm, d, J = 1.6 Hz, 1H; 6.99 ppm, dd, J1 = 1.6 Hz, J2 = 8.0 Hz, 1H; 7.26–7.44 ppm, m, 6H. |
| 48 | —CH₃ | 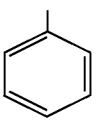 | —C₃H₇ | —CH₂OCH₃ | | (CDCl₃) Base<br>0?85 ppm, m, 3H; 1.4–1.8 ppm, m, 2H; 2.2 ppm, s, 3H; 3.25 ppm, m, 2H; 3.48 ppm, s, 3H 3.9 ppm, s 3H; 4.03 ppm, d, J + 6.5 hz, 2H; 5.66 ppm, t, J = 6.5 Hz, 1H; 7–7.6 ppm, m, 7H. |

TABLE V-continued

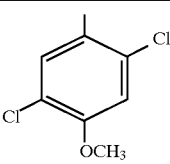

(I)

| EX-AMPLE | R₁ | R₂ | R₃ | R₄ | R₅ | NMR SPECTRUM (SOLVENT) |
|---|---|---|---|---|---|---|
| 49 | —CH₃ | 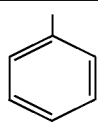 | —C₃H₇ | —CH₂SCH₃ | 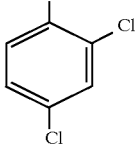 | (CDCl₃) Base<br>0.73 ppm, m, 3H; 1.35–1.60 ppm, m, 2H; 2.18 ppm, 2s, 6H; 3.00–3.08 ppm, m, 2H; 3.19 ppm, d, J = 7.7 Hz; 2H 3.90 ppm, s 2H; 5.62 ppm, t, J = 7.7 Hz, 1H; 6.94 ppm, s, 1H; 7.25–7.43 ppm, m, 6H. |
| 50 | —CH₃ | 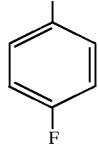 | —C₃H₇ | —CH₂SCH₃ | 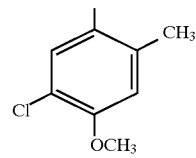 | (CDCl₃) Base<br>0.78 ppm, m, 3H; 1.35–1.60 ppm, m, 2H; 2.16 ppm, s, 3H; 2.18 ppm, s, 3H; 3.00–3.09 ppm, m, 2H 3.18 ppm, d J = 7.7 Hz, 2H; 5.83 ppm, t, J = 7.7 Hz, 1H; 6.99–7.07 ppm, m, 2H; 7.28–7.47 ppm, m, 5H. |
| 51 | —CH₃ | 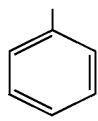 | —C₃H₇ | —CH₂OCH₃ | 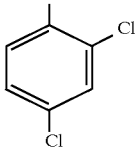 | (CDCl₃) Base<br>0.83 ppm, m, 3H; 1.6 ppm, m, 2H; 2.2 ppm, s, 3H; 2.3 ppm, s, 3H; 3.2 ppm, m, 2H 3.42 ppm, s 3H; 3.9 ppm, s, 3H; 4 ppm, d, J = 6.5 Hz, 2H; 5.61 ppm, t, J = 6.5 Hz, 1H; 6.83 ppm, s, 1H; 7.1–7.5 ppm, m, 8H. |
| 52 | —CH₃ | 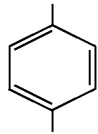 | —C₃H₇ | —CH₂OCH₃ | 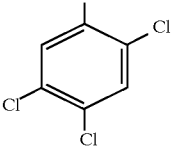 | (CDCl₃) Base<br>0.82 ppm, m, 3H; 1.55 ppm, m, 2H; 2.18 ppm, s, 3H; 3.18 ppm, m, 2H; 3.41 ppm, s, 3H 3.79 ppm, d J = 6.4 Hz, 2H; 5.6 ppm, t, J = 6.4 Hz, 1H; 7–7.1 ppm, m, 2H; 7.2–7.5 ppm, m, 5H. |
| 53 | —CH₃ | 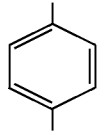 | —C₃H₇ | —CH₂OCH₃ | 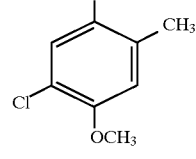 | (CDCl₃) Base<br>0.83 ppm, m, 3H; 1.65 ppm, m, 2H; 2.19 ppm, s, 3H; 3.19 ppm, m, 2H; 3.41 ppm, s, 3H 3.97 ppm, d J = 6.4 Hz, 2H; 5.6 ppm, t, J = 6.4 Hz, 1H; 6.9–7.1 ppm, m, 2H; 7.3–7.45 ppm, m, 2H; 7.55 ppm, s, 2H. |
| 54 | —CH₃ | 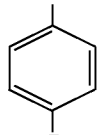 | —C₃H₇ | —CH₂OCH₃ | 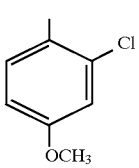 | (CDCl₃) Base<br>0.81 ppm, m, 3H; 1.57 ppm, m, 2H; 2.16 ppm, s, 3H; 2.27 ppm, s, 3H; 3.16 ppm, m, 2H 3.4 ppm, s 3H; 3.88 ppm, s, 3H; 3.95 ppm, d, J = 6.4 Hz, 2H; 5.57 ppm, t, J = 6.4 Hz, 1H; 6.82 ppm, s, 1H; 6.9–7.1 ppm, m, 2H; 7.3–7.5 ppm, m, 3H. |
| 55 | —CH₃ | 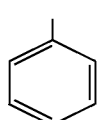 | —C₃H₇ | —CH₂OCH₃ | 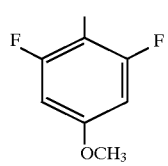 | (CDCl₃) Base<br>0.80 ppm, m, 3H; 1.55 ppm, m, 2H; 2.17 ppm, s, 3H; 3.15 ppm, m, 2H; 3.4 ppm, s, 3H 3.79 ppm, s 3H; 3.96 ppm, d, J = 6.4 Hz, 2H; 5.6 ppm, t, J = 6.4 Hz, 1H; 6.8–7.1 ppm, m, 4H; 7.3–7.5 ppm, m, 3H. |
| 56 | —CH₃ | 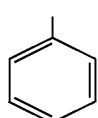 | —C₃H₇ | —CH₂OCH₃ | 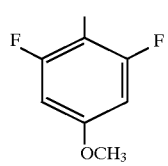 | (CDCl₃) Base<br>0.77 ppm, m, 3H; 1.6 ppm, m, 2H; 2.16 ppm, s, 3H; 3.1 ppm, m, 2H; 3.4 ppm, s, 3H 3.8 ppm, s 3H; 3.94 ppm, d, J = 6.5 Hz, 2H; 5.75 ppm, t, J = 6.5 Hz, 1H; 8.4–8.55 ppm, m, 2H; 6.9–7.05 ppm, m, 2H; 7.35–7.45 ppm, m, 2H. |

TABLE V-continued

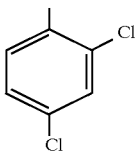

| EXAMPLE | R₁ | R₂ | R₃ | R₄ | R₅ | NMR SPECTRUM (SOLVENT) |
|---|---|---|---|---|---|---|
| 57 | —CH₃ | 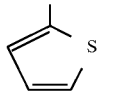 | —C₃H₇ | —CH₂OCH₃ | 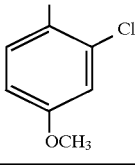 | (CDCl₃) Base 0.9 ppm, m, 3H; 1.67 ppm, m, 2H; 2.2 ppm, s, 3H; 3.2 ppm, m, 2H; 3.44 ppm, s, 3H 3.98 ppm, d J = 6.3 Hz, 2H; 5.9 ppm, t, J = 6.3 Hz, 1H; 6.9–7.5 ppm, m, 6H. |
| 58 | —CH₃ | 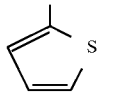 | —C₃H₇ | —CH₂OCH₃ | 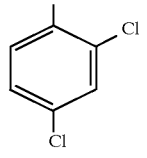 | (CDCl₃) Base 0.86 ppm, m, 3H; 1.60 ppm, m, 2H; 2.18 ppm, s, 3H; 3.2 ppm, m, 2H; 3.43 ppm, s, 3H 3.80 ppm, s, 2H; 3.95 ppm, d, J = 6.3 Hz, 2H; 5.9 ppm, t, J = 6.3 Hz, 1H; 6.82–7.38 ppm, m, 6H. |

The products of Examples 59, 60, 61 and 62 described in Table VI below were respectively obtained from the optically pure (R) and (S) phenylglycines according to Example 16.

Their optical rotations were measured at 20° C. in ethanol.

TABLE VI

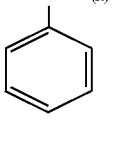

| EXAMPLE | R₁ | R₂ | R₃ | R₄ | R₅ | NMR SPECTRUM (SOLVENT) OR $[\alpha]_D^{20}$ |
|---|---|---|---|---|---|---|
| 59 | —CH₃ | 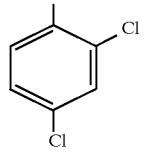 | —C₃H₇ | —CH₂OCH₃ | (R) 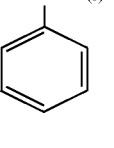 | (CDCl₃) Base 0.78 ppm, t, 3H; 1.18 ppm, t, 3H; 1.50 ppm, m, 2H; 2.15 ppm, s, 3H; 3.17 ppm, m, 2H; 3.55 ppm, q, 2H; 4.0 ppm, d, 2H; 5.54 ppm, t, 1H; 7.26–7.45 ppm, m, 8H. −101 (c = 1.36 C₂H₅OH) |
| 60 | —CH₃ | 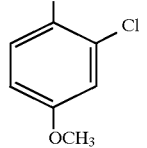 | —C₃H₇ | —CH₂OCH₃ | (S) 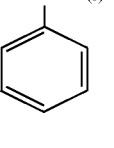 | (CDCl₃) Base 0.8 ppm, t, 3H; 1.6 ppm, m, 2H; 2.17 ppm, s, 3H; 3.15 ppm, m, 2H; 3.42 ppm, s, 3H; 3.97 ppm, d, 2H; 5.59 ppm, t, 1H; 7.20–7.47 ppm, m, 8H. +104.9 (c = 1.19 C₂H₅OH) |
| 61 | —CH₃ | 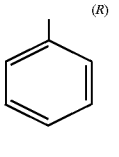 | —C₃H₇ | —CH₂OCH₃ | (R) 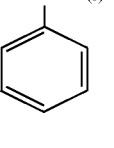 | −109 (c = 1, C₂H₅OH) |

TABLE VI-continued

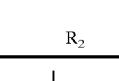

| EXAMPLE | R₁ | R₂ | R₃ | R₄ | R₅ | NMR SPECTRUM (SOLVENT) OR $[\alpha]_D^{20}$ |
|---|---|---|---|---|---|---|
| 62 | —CH₃ | 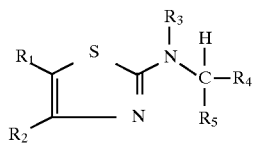 | —C₃H₇ | —CH₂OCH₃ | (S) 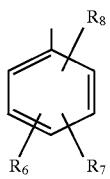 | +109 (c = 1, C₂H₅OH) |

PHARMACEUTICAL PREPARATION

Example 63

Gelatin capsules containing a 20 mg dose of 4-(2,4-dichlorophenyl)-5-methyl-2-[N-(α-ethoxymethylbenzyl)-N-propylamino]thiazole.

4-(2,4-dichlorophenyl)-5-methyl-2-[N-(α-ethoxymethylbenzyl)-N-propylamino]thiazole hydrochloride 20 mg
Corn starch 15 mg
Lactose 25 mg
Talc 5 mg For a No. 3 gelatin capsule

We claim:

1. A method for regulating the secretion of corticotropin (ACTH), β-endorphin, or peptides derived from pro-opiomelanocortin comprising administering to a patient in need thereof an effective amount of a compound of formula I:

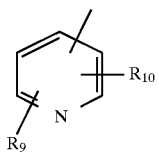 (I)

in which,

R₁ is selected from a hydrogen atom and an alkyl radical of 1 to 5 carbon atoms, R₂ is selected from a radical formula (A):

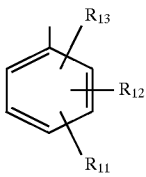 (A)

(in which R₆ represents a hydroxyalkyl radical of 1 to 5 carbon atoms and R₇ and R₈, which may be identical or different, each are selected from hydrogen atom, a halogen atom and a hydroxyalkyl radical of 1 to 5 carbon atoms, a trifluoromethyl, an alkoxy radical of 1 to 5 carbon atoms and an alkyl radical of 1 to 5 carbon atoms), a radical of formula (B):

 (B)

(in which R₉ and R₁₀, which may be identical or different, each are selected from hydrogen atom, a halogen atom, an alkyl radical of 1 to 5 carbon atoms and an alkoxy radical of 1 to 5 carbon atoms), and a radical formula (C):

 (C)

(in which R₁₁, R₁₂ and R₁₃, which may be identical or different, each are selected from a hydrogen atom, a halogen atom, a trifluoromethyl, an alkoxy radical of 1 to 5 carbon atoms and an alkyl radical of 1 to 5 carbon atoms), R₃ is selected from alkyl radical of 1 to 5 carbon atoms, a hydroxyalkyl radical of 1 to 5 carbon atoms, a 2-tetrahydropyranyloxyalkyl radical in which the alkyl radical contains from 1 to 5 carbon atoms, an alkoxyalkyl radical of 2 to 10 carbon atoms and an acyloxyalkyl radical of 3 to 11 carbon atoms, R₄ is selected from a cycloalkyl radical of 3 to 6 carbon atoms, a hydroxyalkyl radical of 1 to 5 carbon atoms, an alkoxyalkyl radical of 2 to 10 carbon atoms, a cycloalkyloxyalkyl radical of 4 to 11 carbon atoms, a hydroxyalkyloxyalkyl radical of 2 to 10 carbon atoms, an acyloxyalkyloxyalkyl radical of 3 to 12 carbon atoms, an acyloxyalkyl radical of 3 to 11 carbon atoms and an alkylthioalkyl radical of 2 to 10 carbon atoms, and, R₅ is selected from a cycloalkyl radical of 3 to 6 carbon atoms, a phenyl radical, a thienyl radical a pyridyl radical (which are optionally substituted with one or more groups selected from halogen atoms, alkoxy radicals of 1 to 5 carbon atoms, alkyl radicals of 1 to 5 carbon atoms and trifluoromethyl radicals), a radical of formula (D):

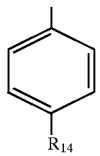

(in which $R_{14}$ is selected from a carboxyl radical, a carboxyalkyl radical of 2 to 6 carbon atoms, an alkoxycarbonyl radical of 2 to 6 carbon atoms, an acyloxyalkyl radical of 3 to 11 carbon atoms where acyl=R'C(O)— and R'=hydrocarbon, an alkoxyalkyl radical of 2 to 10 carbon atoms, an aralkoxyalkyl radical of 8 to 16 carbon atoms (which is optionally substituted on the aromatic ring with one or more groups selected from halogen atoms, alkoxy radicals of 1 to 3 carbon atoms and trifluoromethyl radicals), a monohalo alkyl radical of 1 to 5 carbon atoms, a linear or branched hydroxyalkyl radical of 1 to 5 carbon atoms, a radical of formula (E):

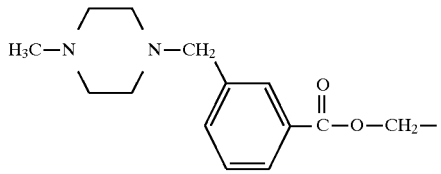

and a sulphooxyalkyl radical of 1 to 5 carbon atoms), a 3-hydroxyalkyl-6-pyridyl radical and a 2-hydroxyalkyl-5-pyridyl radical (in which the alkyl radicals contain from 1 to 5 carbon atoms), on condition, however, that when $R_3$ represents an alkyl radical of 1 to 5 carbon atoms, $R_4$ represents a cycloalkyl radical and $R_5$ is selected from a cycloalkyl radical, a phenyl radical, and a thienyl radical and a pyridyl radical that are optionally substituted with one or more groups selected from halogen atoms, alkoxy radicals of 1 to 5 carbon atoms, alkyl radicals of 1 to 5 carbon atoms and trifluoromethyl radicals, $R_2$ does not represent a radical of formula (C), or a stereoisomer or non-toxic addition salt thereof, associated with a pharmaceutically acceptable carrier.

2. A method of reducing the response to stress comprising administering to a patient in need thereof an effective amount of a compound of formula I:

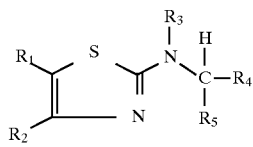

in which, $R_1$ is selected from a hydrogen atom and an alkyl radical of 1 to 5 carbon atoms, $R_2$ is selected from a radical formula (A):

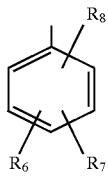

(in which $R_6$ represents a hydroxyalkyl radical of 1 to 5 carbon atoms and $R_7$ and $R_8$ which may be identical or different, each are selected from hydrogen atom, a halogen atom and a hydroxyalkyl radical of 1 to 5 carbon atoms, a trifluoromethyl, an alkoxy radical of 1 to 5 carbon atoms and an alkyl radical of 1 to 5 carbon atoms), a radical of formula (B):

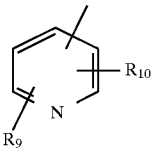

(in which $R_9$ and $R_{10}$, which may be identical or different, each are selected from hydrogen atom, a halogen atom, an alkyl radical of 1 to 5 carbon atoms and an alkoxy radical of 1 to 5 carbon atoms), and a radical formula (C):

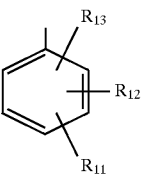

(in which $R_{11}$, $R_{12}$ and $R_{13}$, which may be identical or different, each are selected from a hydrogen atom, a halogen atom, a trifluoromethyl, an alkoxy radical of 1 to 5 carbon atoms and an alkyl radical of 1 to 5 carbon atoms), $R_3$ is selected from alkyl radical of 1 to 5 carbon atoms, a hydroxyalkyl radical of 1 to 5 carbon atoms, a 2-tetrahydropyranyloxyalkyl radical in which the alkyl radical contains from 1 to 5 carbon atoms, an alkoxyalkyl radical of 2 to 10 carbon atoms and an acyloxyalkyl radical of 3 to 11 carbon atoms, $R_4$ is selected from a cycloalkyl radical of 3 to 6 carbon atoms, a hydroxyalkyl radical of 1 to 5 carbon atoms, an alkoxyalkyl radical of 2 to 10 carbon atoms, a cycloalkyloxyalkyl radical of 4 to 11 carbon atoms, a hydroxyalkyloxyalkyl radical of 2 to 10 carbon atoms, an acyloxyalkyloxyalkyl radical of 3 to 12 carbon atoms, an acyloxyalkyl radical of 3 to 11 carbon atoms and an alkylthioalkyl radical of 2 to 10 carbon atoms, and, $R_5$ is selected from a cycloalkyl radical of 3 to 6 carbon atoms, a phenyl radical, a thienyl radical a pyridyl radical (which are optionally substituted with one or more groups selected from halogen atoms, alkoxy radicals of 1 to 5 carbon atoms, alkyl radicals of 1 to 5 carbon atoms and trifluoromethyl radicals), a radical of formula (D):

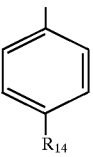

(in which $R_{14}$ is selected from a carboxyl radical, a carboxyalkyl radical of 2 to 6 carbon atoms, an alkoxycarbonyl radical of 2 to 6 carbon atoms, an acyloxyalkyl radical of 3 to 11 carbon atoms where acyl=R'C(O)— and R'=hydrocarbon, an alkoxyalkyl radical of 2 to 10 carbon atoms, an aralkoxyalkyl radical of 8 to 16 carbon atoms (which is optionally substituted on the aromatic ring with one or more groups selected from halogen atoms, alkoxy radicals of 1 to 3 carbon atoms and trifluoromethyl radicals), a monohalo alkyl radical of 1 to 5 carbon atoms, a linear or branched hydroxyalkyl radical of 1 to 5 carbon atoms, a radical of formula (E):

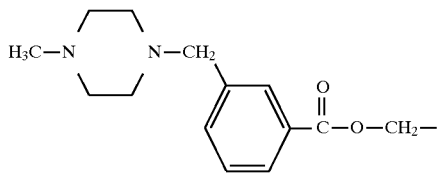

and a sulphooxyalkyl radical of 1 to 5 carbon atoms), a 3-hydroxyalkyl-6-pyridyl radical and a 2-hydroxyalkyl-5-pyridyl radical (in which the alkyl radicals contain from 1 to 5 carbon atoms), on condition, however, that when $R_3$ represents an alkyl radical of 1 to 5 carbon atoms, $R_4$ represents a cycloalkyl radical and $R_5$ is selected from a cycloalkyl radical, a phenyl radical, and a thienyl radical and a pyridyl radical that are optionally substituted with one or more groups selected from halogen atoms, alkoxy radicals of 1 to 5 carbon atoms, alkyl radicals of 1 to 5 carbon atoms and trifluoromethyl radicals, $R_2$ does not represent a radical of formula (C), or a stereoisomer or non-toxic addition salt thereof.

3. A method for the treatment of stress-related behavioral disorders, stress-related emotional states, stress-related gastrointestinal and cardiovascular disorders, and stress-related disorders of the immune system comprising administering to a patient in need thereof an effective amount of a compound of formula I:

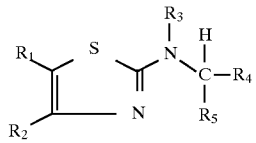

in which, $R_1$ is selected from a hydrogen atom and an alkyl radical of 1 to 5 carbon atoms, $R_2$ is selected from a radical formula (A):
(in which $R_6$ represents a hydroxyalkyl radical of 1 to 5 carbon atoms and $R_7$ and $R_8$ which may be identical or different, each are selected from hydrogen atom, a halogen atom and a hydroxyalkyl radical of 1 to 5 carbon atoms, a trifluoromethyl, an alkoxy radical of 1 to 5 carbon atoms and an alkyl radical of 1 to 5 carbon atoms), a radical of formula (B):
(in which $R_9$ and $R_{10}$, which may be identical or different, each are selected from hydrogen atom, a halogen atom, an alkyl radical of 1 to 5 carbon atoms and an alkoxy radical of 1 to 5 carbon atoms), and a radical formula (C):
(in which $R_{11}$, $R_{12}$ and $R_{13}$, which may be identical or different, each are selected from a hydrogen atom, a halogen atom, a trifluoromethyl, an alkoxy radical of 1 to 5 carbon atoms and an alkyl radical of 1 to 5 carbon atoms), $R_3$ is selected from alkyl radical of 1 to 5 carbon atoms, a hydroxyalkyl radical of 1 to 5 carbon atoms, a 2-tetrahydropyranyloxyalkyl radical in which the alkyl radical contains from 1 to 5 carbon atoms, an alkoxyalkyl radical of 2 to 10 carbon atoms and an acyloxyalkyl radical of 3 to 11 carbon atoms, $R_4$ is selected from a cycloalkyl radical of 3 to 6 carbon atoms, a hydroxyalkyl radical of 1 to 5 carbon atoms, an alkoxyalkyl radical of 2 to 10 carbon atoms, a cycloalkyloxyalkyl radical of 4 to 11 carbon atoms, a hydroxyalkyloxyalkyl radical of 2 to 10 carbon atoms, an acyloxyalkyloxyalkyl radical of 3 to 12 carbon atoms, an acyloxyalkyl radical of 3 to 11 carbon atoms and an alkylthioalkyl radical of 2 to 10 carbon atoms, and, $R_5$ is selected from a cycloalkyl radical of 3 to 6 carbon atoms, a phenyl radical, a thienyl radical a pyridyl radical (which are optionally substituted with one or more groups selected from halogen atoms, alkoxy radicals of 1 to 5 carbon atoms, alkyl radicals of 1 to 5 carbon atoms and trifluoromethyl radicals), a radical of formula (D):

(in which $R_{14}$ is selected from a carboxyl radical, a carboxyalkyl radical of 2 to 6 carbon atoms, an alkoxycarbonyl radical of 2 to 6 carbon atoms, an acyloxyalkyl radical of 3 to 11 carbon atoms where acyl=$R'C(O)$— and $R'$=hydrocarbon, an alkoxyalkyl radical of 2 to 10 carbon atoms, an aralkoxyalkyl radical of 8 to 16 carbon atoms (which is optionally substituted on the aromatic ring with one or more groups selected from halogen atoms, alkoxy radicals of 1 to 3 carbon atoms and trifluoromethyl radicals), a monohalo alkyl radical of 1 to 5 carbon atoms, a linear or branched hydroxyalkyl radical of 1 to 5 carbon atoms, a radical of formula (E):

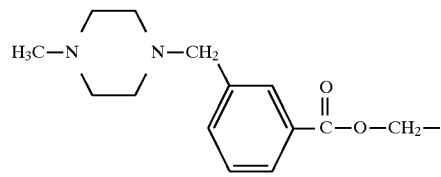

and a sulphooxyalkyl radical of 1 to 5 carbon atoms), a 3-hydroxyalkyl-6-pyridyl radical and a 2-hydroxyalkyl-5-pyridyl radical (in which the alkyl radicals contain from 1 to 5 carbon atoms), on condition, however, that when $R_3$ represents an alkyl radical of 1 to 5 carbon atoms, $R_4$ represents a cycloalkyl radical and $R_5$ is selected from a cycloalkyl radical, a phenyl radical, and a thienyl radical and a pyridyl radical that are optionally substituted with one or more groups selected from halogen atoms, alkoxy radicals of 1 to 5 carbon atoms, alkyl radicals of 1 to 5 carbon atoms and trifluoromethyl radicals, $R_2$ does not represent a radical of formula (C), or a stereoisomer or non-toxic addition salt thereof.

* * * * *